US009993225B2

(12) United States Patent
McMorrow et al.

(10) Patent No.: US 9,993,225 B2
(45) Date of Patent: Jun. 12, 2018

(54) INSTANTANEOUS ULTRASONIC ECHO MEASUREMENT OF BLADDER VOLUME WITH A LIMITED NUMBER OF ULTRASOUND BEAMS

(75) Inventors: Gerald McMorrow, Redmond, WA (US); Henri Baartmans, IJsselstein (NL); Nicolaas Bom, Berkenwoude (NL); Charles Theodoor Lancee, Hoogersmilde (NL)

(73) Assignee: Verathon Inc., Bothell, WA (US)

( * ) Notice: Subject to any disclaimer, the term of this patent is extended or adjusted under 35 U.S.C. 154(b) by 214 days.

(21) Appl. No.: 12/760,291

(22) Filed: Apr. 14, 2010

(65) Prior Publication Data
US 2010/0198075 A1    Aug. 5, 2010

Related U.S. Application Data

(63) Continuation of application No. 11/010,539, filed on Dec. 13, 2004, now Pat. No. 7,749,165, which is a
(Continued)

(51) Int. Cl.
*A61B 8/00* (2006.01)
*A61B 8/08* (2006.01)
(Continued)

(52) U.S. Cl.
CPC .............. *A61B 8/08* (2013.01); *A61B 8/0858* (2013.01); *A61B 8/483* (2013.01);
(Continued)

(58) Field of Classification Search
USPC ........................................ 600/407, 427, 437
See application file for complete search history.

(56) References Cited

U.S. PATENT DOCUMENTS

| 4,431,007 A | 2/1984 | Amazeen et al. ............. 128/660 |
| 4,556,066 A | 12/1985 | Semrow ........................ 128/660 |

(Continued)

FOREIGN PATENT DOCUMENTS

| EP | 0 271 214 | 6/1988 |
| EP | 1 030 187 | 8/2000 |

(Continued)

OTHER PUBLICATIONS

Baker, A., et al.: "Distortion and High-Frequency Generation Due to Nonlinear Propagation of Short Ultrasonic Pulses from a Plane Circular Piston", Journal of Acoustical Society of America, vol. 92, No. 3, pp. 1699-1705, Sep. 1992.
(Continued)

*Primary Examiner* — Jonathan Cwern
(74) *Attorney, Agent, or Firm* — Snyder, Clark, Lesch & Chung, LLP

(57) ABSTRACT

An apparatus and methods to quantify the volume of urine in a human bladder with a limited number of acoustic beams is disclosed. In a first version a plurality of narrow ultrasound beams is transmitted in different directions towards the bladder. Returning echoes are converted to digital form and stored in memory. A volume display on the apparatus allows to define the optimal apposition of the transducer assembly. Signal processing software automatically determines the bladder Depth D and Height H and computes the volume of urine. In a second version, a single wide angle ultrasound beam transducer transmits ultrasounds signals at a fundamental frequency to quantify the urine volume. Return signals originating from a depth beyond the usual position of the posterior wall depth of a filled bladder are analyzed for presence of higher harmonic signals, which in turn are related to the presence or absence of urine.

14 Claims, 10 Drawing Sheets

Related U.S. Application Data continuation of application No. PCT/EP03/07807, filed on Jul. 1, 2003.

(51) Int. Cl.

| | | |
|---|---|---|
| *G01S 7/52* | (2006.01) | |
| *G06T 7/00* | (2017.01) | |
| *G06T 7/62* | (2017.01) | |
| *A61B 5/20* | (2006.01) | |
| *G01S 15/10* | (2006.01) | |
| *G01S 15/89* | (2006.01) | |

(52) U.S. Cl.
CPC ........ *G01S 7/52036* (2013.01); *G06T 7/0012* (2013.01); *G06T 7/62* (2017.01); *A61B 5/204* (2013.01); *A61B 8/4472* (2013.01); *G01S 15/102* (2013.01); *G01S 15/8909* (2013.01); *G06T 2207/10132* (2013.01); *G06T 2207/30004* (2013.01)

(56) References Cited

U.S. PATENT DOCUMENTS

| | | | | |
|---|---|---|---|---|
| 4,733,668 A * | 3/1988 | Torrence | .............. | 600/437 |
| 4,757,821 A | 7/1988 | Snyder | .............. | 128/660 |
| 4,771,205 A | 9/1988 | Mequio | .............. | 310/334 |
| 4,821,210 A | 4/1989 | Rumbaugh | .............. | 364/518 |
| 4,844,080 A | 7/1989 | Frass et al. | .............. | 128/660.01 |
| 4,926,871 A | 5/1990 | Ganguly et al. | .............. | 128/660.07 |
| 5,060,515 A | 10/1991 | Kanda et al. | .............. | 73/602 |
| 5,078,149 A | 1/1992 | Katsumata et al. | .............. | 128/662.03 |
| 5,125,410 A | 6/1992 | Misono et al. | .............. | 128/662.06 |
| 5,148,809 A | 9/1992 | Biegeleisen-Knight et al. | .............. | 128/660.07 |
| 5,151,856 A | 9/1992 | Halmann et al. | .............. | 364/413.03 |
| 5,159,931 A | 11/1992 | Pini | .............. | 128/660.07 |
| 5,197,019 A | 3/1993 | Delon-Martin et al. | .............. | 364/563 |
| 5,265,614 A | 11/1993 | Hayakawa et al. | .............. | 128/602.03 |
| 5,299,577 A | 4/1994 | Brown et al. | .............. | 128/660.07 |
| 5,381,794 A | 1/1995 | Tei et al. | .............. | 128/662.03 |
| 5,432,310 A | 7/1995 | Stoeger | .............. | 200/82 R |
| 5,435,310 A | 7/1995 | Sheehan et al. | .............. | 128/653.1 |
| 5,465,721 A | 11/1995 | Kishimoto et al. | .............. | 128/660.07 |
| 5,473,555 A | 12/1995 | Potter | .............. | 364/724.1 |
| 5,487,388 A | 1/1996 | Rello et al. | .............. | 128/660.09 |
| 5,503,152 A | 4/1996 | Oakley et al. | .............. | 128/661.01 |
| 5,503,153 A | 4/1996 | Liu et al. | .............. | 128/661.08 |
| 5,526,816 A | 6/1996 | Arditi | .............. | 128/662.02 |
| 5,553,618 A | 9/1996 | Suzuki et al. | .............. | 128/653.1 |
| 5,575,286 A | 11/1996 | Weng et al. | .............. | 128/653.1 |
| 5,575,291 A | 11/1996 | Hayakawa et al. | .............. | 128/662.03 |
| 5,577,506 A | 11/1996 | Dias | .............. | 128/662.03 |
| 5,588,435 A | 12/1996 | Weng et al. | .............. | 128/660.07 |
| 5,601,084 A | 2/1997 | Sheehan et al. | .............. | 128/661.04 |
| 5,605,155 A | 2/1997 | Chalana et al. | .............. | 128/660.07 |
| 5,615,680 A | 4/1997 | Sano | .............. | 128/661.09 |
| 5,644,513 A | 7/1997 | Rudin et al. | .............. | 364/572 |
| 5,645,077 A | 7/1997 | Foxlin | .............. | 128/774 |
| 5,697,525 A | 12/1997 | O'Reilly et al. | .............. | 222/105 |
| 5,698,549 A | 12/1997 | Steers et al. | .............. | 514/211 |
| 5,724,101 A | 3/1998 | Haskin | .............. | 348/441 |
| 5,735,282 A | 4/1998 | Hossack | .............. | 128/662.03 |
| 5,738,097 A | 4/1998 | Beach et al. | .............. | 128/661.09 |
| 5,776,063 A | 7/1998 | Dittrich et al. | .............. | 600/408 |
| 5,782,767 A | 7/1998 | Pretlow, III | .............. | 600/443 |
| 5,806,521 A | 9/1998 | Morimoto et al. | .............. | 128/661.01 |
| 5,841,889 A | 11/1998 | Seyed-Bolorforosh | .............. | 382/128 |
| 5,846,202 A | 12/1998 | Ramamurthy et al. | .............. | 600/450 |
| 5,851,186 A | 12/1998 | Wood et al. | .............. | 600/437 |
| 5,873,829 A | 2/1999 | Kamiyama et al. | .............. | 600/443 |
| 5,892,843 A | 4/1999 | Zhou et al. | .............. | 382/176 |
| 5,898,793 A | 4/1999 | Karron et al. | .............. | 382/131 |
| 5,903,664 A | 5/1999 | Hartley et al. | .............. | 382/154 |
| 5,908,390 A | 6/1999 | Matsushima | .............. | 600/447 |
| 5,928,151 A * | 7/1999 | Hossack et al. | .............. | 600/443 |
| 5,945,770 A | 8/1999 | Hanafy | .............. | 310/322 |
| 5,971,923 A | 10/1999 | Finger | .............. | 600/437 |
| 5,972,023 A | 10/1999 | Tanner et al. | .............. | 606/219 |
| 5,980,459 A | 11/1999 | Chiao et al. | .............. | 600/447 |
| 5,993,390 A | 11/1999 | Savord et al. | .............. | 600/437 |
| 6,008,813 A | 12/1999 | Lauer et al. | .............. | 345/424 |
| 6,030,344 A | 2/2000 | Guracar et al. | .............. | 600/447 |
| 6,042,545 A | 3/2000 | Hossack et al. | .............. | 600/443 |
| 6,048,312 A | 4/2000 | Ishrak et al. | .............. | 600/443 |
| 6,064,906 A | 5/2000 | Langberg et al. | .............. | 600/518 |
| 6,102,858 A | 8/2000 | Hatfield et al. | .............. | 600/443 |
| 6,106,465 A | 8/2000 | Napolitano et al. | .............. | 600/443 |
| 6,117,080 A | 9/2000 | Schwartz | .............. | 600/443 |
| 6,122,538 A | 9/2000 | Sliwa, Jr. et al. | .............. | 600/407 |
| 6,123,669 A | 9/2000 | Kanda | .............. | 600/443 |
| 6,126,598 A | 10/2000 | Entrekin et al. | .............. | 600/437 |
| 6,148,095 A | 11/2000 | Prause et al. | .............. | 382/131 |
| 6,151,404 A | 11/2000 | Pieper | .............. | 382/128 |
| 6,159,150 A | 12/2000 | Yale et al. | .............. | 600/437 |
| 6,171,248 B1 | 1/2001 | Hossack et al. | .............. | 600/459 |
| 6,193,657 B1 | 2/2001 | Drapkin | .............. | 600/437 |
| 6,200,266 B1 | 3/2001 | Shokrollahi et al. | .............. | 600/438 |
| 6,210,327 B1 | 4/2001 | Brackett et al. | .............. | 600/437 |
| 6,213,949 B1 * | 4/2001 | Ganguly et al. | .............. | 600/449 |
| 6,233,480 B1 | 5/2001 | Hochman et al. | .............. | 600/476 |
| 6,238,344 B1 | 5/2001 | Gamelsky et al. | .............. | 600/437 |
| 6,248,070 B1 | 6/2001 | Kanda et al. | .............. | 600/443 |
| 6,254,539 B1 | 7/2001 | Pang et al. | .............. | 600/443 |
| 6,264,609 B1 | 7/2001 | Herrington et al. | .............. | 600/443 |
| 6,272,469 B1 | 8/2001 | Koritzinsky et al. | .............. | 705/2 |
| 6,277,073 B1 | 8/2001 | Bolorforosh et al. | .............. | 600/437 |
| 6,302,845 B2 | 10/2001 | Shi et al. | .............. | 600/438 |
| 6,309,353 B1 | 10/2001 | Cheng et al. | .............. | 600/437 |
| 6,325,758 B1 | 12/2001 | Carol et al. | .............. | 600/439 |
| 6,338,716 B1 | 1/2002 | Hossack et al. | .............. | 600/459 |
| 6,343,936 B1 | 2/2002 | Kaufman et al. | .............. | 434/262 |
| 6,346,124 B1 | 2/2002 | Geiser et al. | .............. | 660/450 |
| 6,350,239 B1 | 2/2002 | Ohad et al. | .............. | 600/437 |
| 6,359,190 B1 | 3/2002 | Ter-Ovanesyan et al. | ... | 604/361 |
| 6,360,027 B1 | 3/2002 | Hossack et al. | .............. | 382/294 |
| 6,375,616 B1 | 4/2002 | Soferman et al. | .............. | 600/443 |
| 6,400,848 B1 | 6/2002 | Gallagher | .............. | 382/254 |
| 6,402,762 B2 | 6/2002 | Hunter et al. | .............. | 606/130 |
| 6,409,665 B1 | 6/2002 | Scott et al. | .............. | 600/437 |
| 6,440,071 B1 | 8/2002 | Slayton et al. | .............. | 600/437 |
| 6,440,072 B1 | 8/2002 | Schuman et al. | .............. | 600/437 |
| 6,443,894 B1 | 9/2002 | Sumanaweera et al. | ..... | 600/443 |
| 6,468,218 B1 | 10/2002 | Chen et al. | .............. | 600/443 |
| 6,485,423 B2 | 11/2002 | Angelsen et al. | .............. | 600/458 |
| 6,494,841 B1 | 12/2002 | Thomas et al. | .............. | 600/447 |
| 6,511,325 B1 | 1/2003 | Lalka et al. | .............. | 434/272 |
| 6,511,426 B1 | 1/2003 | Hossack et al. | .............. | 600/437 |
| 6,511,427 B1 | 1/2003 | Sliwa, Jr. et al. | .............. | 600/438 |
| 6,515,657 B1 | 2/2003 | Zanelli | .............. | 345/419 |
| 6,524,249 B2 | 2/2003 | Moehring et al. | .............. | 600/438 |
| 6,535,759 B1 | 3/2003 | Epstein et al. | .............. | 600/547 |
| 6,540,679 B2 | 4/2003 | Slayton et al. | .............. | 600/439 |
| 6,544,179 B1 | 4/2003 | Schmiesing et al. | .............. | 600/447 |
| 6,545,678 B1 | 4/2003 | Ohazama | .............. | 345/427 |
| 6,565,512 B1 | 5/2003 | Ganguly et al. | .............. | 600/449 |
| 6,569,097 B1 | 5/2003 | McMorrow et al. | .............. | 600/437 |
| 6,569,101 B2 | 5/2003 | Quistgaard et al. | .............. | 600/459 |
| 6,575,907 B1 | 6/2003 | Soferman et al. | .............. | 600/438 |
| 6,585,647 B1 | 7/2003 | Winder | .............. | 600/437 |
| 6,610,013 B1 | 8/2003 | Fenster et al. | .............. | 600/439 |
| 6,611,141 B1 | 8/2003 | Schulz et al. | .............. | 324/226 |
| 6,622,560 B2 | 9/2003 | Song et al. | .............. | 73/606 |
| 6,628,743 B1 | 9/2003 | Drummond et al. | .............. | 378/8 |
| 6,643,533 B2 | 11/2003 | Knoplioch et al. | .............. | 600/407 |
| 6,650,927 B1 | 11/2003 | Keidar | .............. | 600/424 |
| 6,688,177 B2 | 2/2004 | Wiesauer | .............. | 73/618 |
| 6,695,780 B1 | 2/2004 | Nahum et al. | .............. | 600/437 |
| 6,716,175 B2 | 4/2004 | Geiser et al. | .............. | 600/450 |
| 6,752,762 B1 | 6/2004 | DeJong et al. | .............. | 600/458 |
| 6,755,787 B2 | 6/2004 | Hossack et al. | .............. | 600/447 |
| 6,768,811 B2 | 7/2004 | Dinstein et al. | .............. | 382/128 |
| 6,780,152 B2 | 8/2004 | Ustuner et al. | .............. | 600/443 |
| 6,788,620 B2 | 9/2004 | Shiraishi et al. | .............. | 367/152 |

(56) References Cited

U.S. PATENT DOCUMENTS

| | | | |
|---|---|---|---|
| 6,801,643 B2 | 10/2004 | Pieper | 382/128 |
| 6,822,374 B1 | 11/2004 | Smith et al. | 310/334 |
| 6,825,838 B2 | 11/2004 | Smith et al. | 345/419 |
| 6,831,394 B2 | 12/2004 | Baumgartner et al. | 310/334 |
| 6,868,594 B2 | 3/2005 | Gururaja | 29/25.35 |
| 6,884,217 B2 | 4/2005 | McMorrow et al. | 600/443 |
| 6,903,813 B2 | 6/2005 | Jung et al. | 356/73 |
| 6,905,467 B2 | 6/2005 | Bradley et al. | 600/443 |
| 6,905,468 B2 | 6/2005 | McMorrow et al. | 600/443 |
| 6,936,009 B2 | 8/2005 | Venkataramani et al. | 600/459 |
| 6,939,301 B2 | 9/2005 | Abdelhak | 600/437 |
| 6,951,540 B2 | 10/2005 | Ebbini et al. | 600/437 |
| 6,954,406 B2 | 10/2005 | Jones | 367/152 |
| 6,961,405 B2 | 11/2005 | Scherch | 378/65 |
| 6,962,566 B2 | 11/2005 | Quistgaard et al. | 600/437 |
| 7,025,725 B2 | 4/2006 | Dione et al. | 600/443 |
| 7,042,386 B2 | 5/2006 | Woodford et al. | 342/25 |
| 7,087,022 B2 | 8/2006 | Chalana et al. | 600/449 |
| 7,141,020 B2 | 11/2006 | Poland et al. | 600/447 |
| 7,142,905 B2 | 11/2006 | Slayton et al. | 600/427 |
| 7,177,677 B2 | 2/2007 | Kaula et al. | 600/546 |
| 7,189,205 B2 | 3/2007 | McMorrow et al. | 600/437 |
| 7,215,277 B2 | 5/2007 | Woodford et al. | 342/25 F |
| 7,255,678 B2 | 8/2007 | Mehi et al. | 600/446 |
| 7,301,636 B2 | 11/2007 | Jung et al. | 356/402 |
| 7,382,907 B2 | 6/2008 | Luo et al. | 382/128 |
| 7,450,746 B2 | 11/2008 | Yang et al. | 382/131 |
| 7,520,857 B2 | 4/2009 | Chalana et al. | 600/446 |
| 7,611,466 B2 | 11/2009 | Chalana et al. | 600/443 |
| 2001/0031920 A1 | 10/2001 | Kaufman et al. | 600/431 |
| 2002/0005071 A1 | 1/2002 | Song et al. | 73/606 |
| 2002/0016545 A1 | 2/2002 | Quistgaard et al. | 600/437 |
| 2002/0072671 A1 | 6/2002 | Chenal et al. | 600/450 |
| 2002/0133075 A1 | 9/2002 | Abdelhak | 600/443 |
| 2002/0165448 A1 | 11/2002 | Ben-Haim et al. | 600/424 |
| 2003/0055336 A1* | 3/2003 | Buck et al. | 600/453 |
| 2003/0142587 A1 | 7/2003 | Zeitzew | 367/127 |
| 2003/0174872 A1 | 9/2003 | Chalana et al. | 382/128 |
| 2003/0181806 A1 | 9/2003 | Medan et al. | 600/411 |
| 2003/0216646 A1 | 11/2003 | Angelsen et al. | 600/437 |
| 2003/0229281 A1 | 12/2003 | Barnard et al. | 600/438 |
| 2004/0006266 A1 | 1/2004 | Ustuner et al. | 600/47 |
| 2004/0024302 A1 | 2/2004 | Chalana et al. | 600/407 |
| 2004/0034305 A1 | 2/2004 | Song et al. | 600/447 |
| 2004/0054280 A1 | 3/2004 | McMorrow et al. | 600/443 |
| 2004/0076317 A1 | 4/2004 | Roberts | 328/128 |
| 2004/0106869 A1 | 6/2004 | Tepper | 600/443 |
| 2004/0127797 A1 | 7/2004 | Barnard et al. | 600/449 |
| 2004/0267123 A1 | 12/2004 | McMorrow et al. | 600/443 |
| 2005/0135707 A1 | 6/2005 | Turek et al. | 382/294 |
| 2005/0174324 A1 | 8/2005 | Liberty et al. | 345/156 |
| 2005/0193820 A1 | 9/2005 | Sheljaskow et al. | 73/649 |
| 2005/0212757 A1 | 9/2005 | Marvit et al. | 345/156 |
| 2005/0215896 A1 | 9/2005 | McMorrow et al. | 600/437 |
| 2005/0228276 A1 | 10/2005 | He et al. | 600/437 |
| 2005/0240126 A1 | 10/2005 | Foley et al. | 601/2 |
| 2005/0253806 A1 | 11/2005 | Liberty et al. | 345/156 |
| 2006/0025689 A1 | 2/2006 | Chalana et al. | 600/456 |
| 2006/0064010 A1 | 3/2006 | Cannon, Jr. et al. | 600/434 |
| 2006/0078501 A1 | 4/2006 | Goertz et al. | 424/9.52 |
| 2006/0079775 A1 | 4/2006 | McMorrow et al. | 600/443 |
| 2006/0111633 A1 | 5/2006 | McMorrow et al. | 600/437 |
| 2006/0235301 A1 | 10/2006 | Chalana et al. | 600/443 |
| 2007/0004983 A1 | 1/2007 | Chalana et al. | 600/443 |
| 2007/0232908 A1 | 10/2007 | Wang et al. | 600/437 |
| 2007/0276247 A1 | 11/2007 | Chalana et al. | 600/447 |
| 2007/0276254 A1 | 11/2007 | Yang et al. | 600/463 |
| 2008/0139938 A1 | 6/2008 | Yang et al. | 600/445 |
| 2008/0146932 A1 | 6/2008 | Chalana et al. | 600/447 |
| 2008/0242985 A1 | 10/2008 | Chalana et al. | 600/443 |
| 2008/0249414 A1 | 10/2008 | Yang et al. | 600/445 |
| 2008/0262356 A1 | 10/2008 | Chalana et al. | 600/447 |
| 2009/0062644 A1 | 3/2009 | McMorrow et al. | 600/437 |
| 2009/0088660 A1 | 4/2009 | McMorrow et al. | 600/546 |
| 2009/0105585 A1 | 4/2009 | Wang et al. | 600/437 |
| 2009/0112089 A1 | 4/2009 | Barnard et al. | 600/443 |
| 2009/0264757 A1 | 10/2009 | Yang et al. | 600/443 |

FOREIGN PATENT DOCUMENTS

| | | |
|---|---|---|
| EP | 1 076 318 | 2/2001 |
| JP | 2000-126178 | 5/2000 |
| JP | 2000-126181 | 5/2000 |
| JP | 2000-126182 | 5/2000 |
| WO | 01/35339 | 5/2001 |
| WO | 2009/032778 | 3/2009 |

OTHER PUBLICATIONS

Baker, A., et al., "Prediction of Non-Linear Propagation in Water Due to Diagnostic Medical Ultrasound Equipment", Phys. Med Biol., vol. 36, No. 11, pp. 1457-1464, 1991.

Barentsz et al., "Primary Staging of Urinary Bladder Carcinoma: the Role of MRI and a Comparison with CT," European Radiology vol. 6, pp. 129-133, 1996.

Besl, P., et al., "A Method for Registration of 3-D Shapes," IEEE Transaction on Pattern Analysis and Machine Intelligence, vol. 14, No. 2, pp. 239-256, Feb. 1992.

Birnholz, J., et al., "Amniotic Fluid Accumulation in the First Trimester," American Institute of Ultrasound in Medicine, Journal Ultrasound Medicine, vol. 14, pp. 597-602, 1995.

Bishop, S., et al., "Human Tissue-Temperature Rise During Ultrasound Treatments with the Aquaflex Gel Pad." Journal of Athletic Training, vol. 39, No. 2, pp. 126-131, 2004.

Bouakaz, A., et al., "Noninvasive Bladder Volume Measurements Based on Nonlinear Wave Distortion," Ultrasound in Medicine & Biology, vol. 30, No. 4, pp. 469-476, 2004.

Boyle, P., et al, "Prostate Volume Predicts Outcome of Treatment of Benign Prostatic Hyperplasia with Finasteride: Meta-Analysis of Randomized Clinical Trials," Urology, vol. 48, No. 3, pp. 398-405, 1996.

Cascione, C., et al., "Transabdominal Ultrasound Versus Excretory Urography in Preoperative Evaluation of Patients with Prostatism," The Journal of Urology, vol. 137, pp. 883-885, May 1987.

Chamberlain, P., "Amniotic Fluid Volume: Ultrasound Assessment and Clinical Significance," Seminars in Perinatology, vol. 9, No. 4, pp. 163-167, 1985.

Chamberlain, P. "Ultrasound Evaluation of Amniotic Fluid Volume," American Journal of Obstetrics and Gynaecology, vol. 150, No. 3, pp. 250-254, Oct. 1, 1984.

Cheng, X. et al., "Boundary Extraction Method for Three Dimensional Ultrasonic Echo Imaging Using Fuzzy Reasoning and Relaxation Techniques," IEEE, pp. 1610-1614, 1994.

Christensen, M., et al., "Clinical Manifestations of Benign Prostatic Hyperplasia and Indications for Therapeutic Intervention," Benign Prostatic Hyperplasia, Urologic Clinics of North America, vol. 17, No. 3, pp. 509-516, Aug. 1990.

Crowley, P., et al., "The Value of Ultrasound Measurement of Amniotic Fluid Volume in the Management of Prolonged Pregnancies," British Journal of Obstetrics and Gynaecology, vol. 91, pp. 444-448, May 1984.

Cvitkovic-Kuzmic, A., et al., "Sonographic Measurement of Detrusor Muscle Thickness in Healthy Children," Pedatric Nephrology, vol. 16, pp. 1122-1125, 2001.

Cvitkovic-Kuzmic, A., et al., "Ultrasound Assessment of Detrusor Muscle Thickness in Children with Non-Neuropathic Bladder/Sphincter Dysfunction," European Urology, Vo. 41, pp. 214-219, 2002.

Elliott, P., "Interactive Image Segmentation for Radiation Treatment Planning," IBM Systems Journal, vol. 31, No. 4, pp. 620-634, 1992.

Forbes, F., et al., "Bayesian Morphology: Fast Unsupervised Bayesian Image Analysis," Journal of the American Statistical Association, vol. 94, No. 446, pp. 555-568, Jun. 1999.

Gramellini, D., et al., "Sonographic Assessment of Amniotic Fluid Volume Between 11 and 24 Weeks of Gestation: Construction of Reference Intervals Related to Gestational Age," Ultrasound Obstetrics Gynaecology, vol. 17, pp. 410-415, 2001.

(56) References Cited

OTHER PUBLICATIONS

Grover, J., et al., "Three-Dimensional Method for Determination of Amniotic Fluid Volume in Intrauterine Pockets," vol. 90, No. 6, pp. 1007-1010, Dec. 1997.

Hakenberg, O., et al., "Bladder Wall Thickness in Normal Adults and Men with Mild Lower Urinary Tract Symptoms and Benign Prostatic Enlargement," Neurourology and Urodynamics, vol. 19, pp. 585-593, 2000.

Hakenberg, O., et al., "The Estimation of Bladder Volume by Sonocystrography," Journal of Urology, vol. 130, No. 2, pp. 249-251, Aug. 1983.

Holmes, J., et al., "Ultrasonic Studies of the Bladder," The Journal of Urology, vol. 91, pp. 654-663, 1967.

Jeng, C., et al., "Amniotic Fluid Index Measurement with the Four-Quadrant Technique During Pregnancy," The Journal of Reproductive Medicine, Inc., vol. 35, No. 7, pp. 674-677, Jul. 1990.

Jequier, S., et al., "Sonographic Measurements of the Normal Bladder Wall in Children," AJR, vol. 149, pp. 563-566, Sep. 1987.

Khullar, V., et al. "A Novel Technique for Measuring Bladder Wall Thickness in Women Using Transvaginal Ultrasound," Ultrasound Obestetrics and Gyneacology, vol. 4, pp. 220-223, 1994.

Khullar, V., et al., "Ultrasound: a Noninvasive Screening Test for Detrusor Instability," British Journal of Obstetrics and Gynaecology, vol. 103, pp. 904-908, Sep. 1996.

Kojima, M., et al., "Reversible Change of Bladder Hypertrophy Due to Benign Prostatic Hyperplasia After Surgical Relief of Obstruction," The Journal of Urology, vol. 158, pp. 89-93, Jul. 1997.

Kojima, M., et al., "Ultrasonic Estimation of Bladder Weight as a Measure of Bladder Hypertrophy in Men with Infravesical Obstruction: a Preliminary Report," Urology, vol. 47, No. 6, pp. 942-947, 1996.

Krenning, B., et al., "Assessment of Left Ventricular Function by Three-Dimensional Echocardiography," Cardiovascular Ultrasound, 7 pgs., 2003.

Lea, J., et al., "Registration and Immobilization in Robot-Assisted Surgery," Computer Aided Surgery, vol. 1, No. 2, pp. 80-87, 1995.

Lorensen, W., et al., "Marching Cubes: A High Resolution 3D Surface Construction Algorithm," ACM Siggraph Computer Graphics, vol. 21, No. 4, pp. 163-169, Jul. 1987.

Madsen, F., et al., "Clinical Manifestations of Benign Prostatic Hyperplasia," Advances in Benign Prostatic Hyperplasia, Urologic Clinics of North America, vol. 22, No. 2, pp. 291-298, May 1995.

Magann, E., et al., "Amniotic Fluid Volume Determination," American Journal of Obstetrics and Gyneacology, Vo. 169, No. 2, Part 1, pp. 435-437, 1999.

Magann, E., et al., "Measurement of Amniotic Fluid Volume: Accuracy of Ultrasonography Techniques," American Journal of Obstetrics and Gyneacology, vol. 167, No. 6, pp. 1533-1537, 1992.

Magann, E., et al., "Ultrasound Estimate of Amniotic Fluid Volume: Color Doppler Overdiagnosis of Oligohydramnios," Obstetrics & Gynecology, vol. 98, No. 1, pp. 71-74, Jul. 2001.

Magann, E., et al., "Ultrasound Estamation of Amniotic Fluid Volume Using the Largest Vertical Pocket Containing Umbilical Cord: Measure to or Through the Cord," Ultrasound Obstetrics and Gynecology, vol. 20, pp. 464-467, 2002.

Manieri, C., et al., "The Diagnosis of Bladder Outlet Obstruction in Men by Ultrasound Measurement of Bladder Wall Thickness," The Journal of Urology, vol. 159, 761-765, pp. 761-765, Mar. 1998.

Mann, S., et al., "Novel Technique for Assessing Amniotic Fluid Volume: use of a Three-Dimensional Bladder Scanner," The Journal of Maternal-Fetal Medicine, vol. 9, pp. 308-310, 2000.

Manning, F., et al., "Qualitative Amniotic Fluid Volume Determination by Ultrasound: Antepartum Detection of Intrauterine Growth Retardation," American Journal of Obstetrics and Gynecology, vol. 139, No. 3, pp. 254-258, Feb. 1, 1981.

Martan, A., et al., "Ultrasound Imaging of the Lower Urinary System in Women after Burch Colposuspension," Ultrasound Obstetrics and Gynecology, vol. 17, pp. 58-64, 2001.

Matthews, P. et al., "The Use of Ultrasound in the Investigation of Prostatism," British Journal of Urology, vol. 54, pp. 536-538, 1982.

Merks, E. et al., "Design of a Multilayer Transducer for Acoustic Bladder Volume Assessment," IEEE Transacations on Ultrasonics, Ferroelectrics and Frequency Control, vol. 53, No. 10, pp. 1730-1738, Oct. 2006.

Merks, E., et al., "A KLM-Circuit Model of a Multi-Layer Transducer for Acoustic Bladder Volume Measurements," Ultrasonics, vol. 44, pp. 705-710, Dec. 22, 2006.

Miyashita, H., et al., "Ultrasonic Measurement of Bladder Weight as a Possible Predictor of Acute Urinary Retention in Men with Lower Urinary Tract Symptoms Suggestive of Benign Prostatic Hyperplasia," Ultrasound in Medicine & Biology, vol. 28, No. 8, pp. 985-990, 2002.

Moore, T., "Superiority of the Four-Quadrant Sum Over the Single-Deepest-Pocket Technique in Ultrasonographic Identification of Abnormal Amniotic Fluid Volumes," American Journal of Obstetrics and Gynecology, vol. 163, No. 5, pp. 762-767, 1990.

Muller, L., et al., "Detrusor Thickness in Healthy Children Assessed by a Standardized Ultrasound Method," The Journal of Urology, vol. 166, pp. 2364-2367, Dec. 2001.

Muller, L., et al., "Standardized Ultrasound Method for Assessing Detrusor Muscle Thickness in Children," The Journal of Urology, vol. 164, pp. 134-138, Jul. 2000.

Myles, T., et al., "Four-Quadrant Assessment of Amniotic Fluid Volume: Distribution's Role in Predicting Fetal Outcome," Journal of Obstetrics and Gynecology, vol. 80, No. 5, pp. 769-774, Nov. 1992.

Naya, Y., et al., "Intraobserver and Interobserver Variance in the Measurement of Ultrasound-Estimated Bladder Weight," Ultrasound in Medicine and Biology, vol. 24, No. 5, pp. 771-773, 1998.

Oelke, M., et al., "Increase in Detrusor Wall Thickness Indicates Bladder Outlet Obstruction (BOO) in Men," World Journal of Urology, vol. 19, pp. 443-452, 2002.

Ohashit, G., et al., "Boundary Estimation for Ultrasonic 3-D Imaging," SPIE vol. 1898 Image Processing, pp. 480-486, 1993.

Oomen, JA, et al., "Towards Assessment of Regional Wall Stress of the Left Ventricle Using 3D Ultrasound Imaging," IEEE Computers in Cardiology, vol. 26, pp. 129-132, 1999.

Phelan, J., et al., Amniotic Fluid Volume Assessment with the Four-Quadrant Technique at 36-42 Weeks Gestation, The Journal of Reproductive Medicine, vol. 32, No. 7, pp. 540-542, Jul. 1987.

Rutherford, S., et al., "The Four-Quadrant Assessment of Amniotic Fluid Volume: An Adjunct to Antepartum Fetal Heart Rate Testing," Journal of Obstetrics and Gynecology, vol. 70, No. 3, Part 1, pp. 353-356, Sep. 1987.

Sagiv, C., et al., "Application of a Semiautomatic Boundary Detection Algorithm for the Assessment of Amniotic Fluid Quantity Form Ultrasound Images," Ultrasound in Medicine and Biology, vol. 25, No. 4, pp. 515-526, 1999.

Sahin, B., et al., "Estimation of the Amniotic Fluid Volume Using the Cavalieri Method on Ultrasound Images," International Journal of Gynecology and Obstetrics, vol. 82, pp. 25-30, 2003.

Santilli, J., et al., "Diagnosis and Treatment of Abdominal Aortic Aneurysms," American Family Physician, vol. 56, No. 4, pp. 1081-1090, Sep. 1997.

Scheinerman, E., "Invitation to Dynamical Systems," Chapter 5, 'Fractals,' Prentice Hall pp. 231-315, 1996.

Schiff, E., et al., "Standardized Measurement of Amniotic Fluid Volume by Correlation of Sonography with Dye Dilution Technique," Obestetrics and Gynecology, vol. 76, No. 1, pp. 44-46, Jul. 1990.

Schrimmer, D., et al., "Sonographic Evaluation of Amniotic Fluid Volume," Clinical Obstetrics and Gynecology, vol. 45, No. 4, pp. 1026-1029, 2002.

Sepulveda W., et al., "Direct Volume Measurement at Midtrimester Amnioinfusion in Relation to Ultrasonographic Indexes of Amniotic Fluid Volume," American Journal of Obstetrics and Gynecology, vol. 170, No. 4, pp. 1160-1163, Apr. 1994.

Shiota, T., et al., "Real-time Three-Dimensional Echocardiography for Determining Right Ventricular Stroke Volume in an Animal Model of Chronic Right Ventricular Volume Overload," Circulation Journal of the American Heart Association, vol. 97, pp. 1897-1900, 1998.

(56) References Cited

OTHER PUBLICATIONS

Stangenberg, M., et al., "Amniotic Fluid Volumes in Pregnant Diabetics During the Last Trimester," Acta Obstetrics Gynecology Scand, vol. 61, pp. 313-316, 1982.
Szabo, T., et al., "Effects of Nonlinearity on the Estimation of In Situ Values of Acoustic Output Parameters," Journal of Ultrasound in Medicine, American Institute of of Ultrasound in Medicine, vol. 18, No. 1, pp. 33-41, 1999.
Weissman, A., et al., "Sonographic Measurement of Amniotic Fluid Volume in the First Trimester of Pregnancy," American Institute of Ultrasound in Medicine, vol. 15, pp. 771-774, 1996.
Gerald, C., et al., "Applied Numerical Analysis," Fifth Edition, Addison-Wesley Publishing Company, Chapter 3, "Interpolation and Curve Fitting," pp. 210-287, 1994.
Gobbi, D., et al., "Real-Time 3D Ultrasound for Intraoperative Surgical Guidance," 8 pgs, Jan. 2001.
De Jong, Nico, et al., "Ultrasound Contrast Agents" ISBN 1-85317-858-4, Chapter 3, "Contrast-Specific Imaging Methods," 12 pages, 2001.
Kruczkowski, Philip J.C., et al., "A Non-Invasive Ultrasonic System to Determine Residual Bladder Volumes," IEEE Engineering in Medicine Biology Society 10th Annual International Conference, pp. 1623-1624, 1988.

* cited by examiner

Fig. 2 Various, filling dependent measurement configurations.

INSTANTANEOUS ULTRASONIC ECHO MEASUREMENT OF BLADDER VOLUME WITH A LIMITED NUMBER OF ULTRASOUND BEAMS

PRIORITY CLAIM

This application is a continuation of application Ser. No. 11/010,539 U.S. Pat. No. 7,749,165, which claims priority to PCT/EP2003/007807 filed Jul. 1, 2003, which application claims priority to UK Patent Application No. GB 2 391 625A filed Aug. 9, 2002. Each of the foregoing applications is incorporated by reference as if fully set forth herein.

The present invention relates to methods and apparatus for the measurement of volume of a fluid filled cavity in a human or animal body, such as a bladder, using ultrasound techniques.

TECHNICAL FIELD

This invention concerns an apparatus which, in a first version, with a limited number of fixed ultrasound transducers with narrow sound beams oriented in well defined directions, automatically determines the volume of the human bladder without assumption of any geometrical bladder shape, where volume is calculated by (Height×Depth× K) and the empirically measured K factor varies with bladder filling degree, which in turn is indicated by the number of ultrasonic beams that intercept the filled bladder. In this first version, standard echographic technique is used where short ultrasound pulses are transmitted at fundamental frequency and the echo travel time is used to calculate distance.

In a second version, with a wide ultrasound beam, pulses are transmitted at fundamental frequency. Due to the wide sound beam this beam encompasses a large part of the volume of a possibly filled bladder. Echo signals from a large distance W, where W is the average distance from the transducer in dorsal direction to a point beyond the posterior wall of an average filled bladder, are analyzed for higher harmonic contents. Non-linear behavior will increase with depth and particularly be stimulated by presence of urine. Attenuation of returned echo signals from a large distance will be considerably less in the presence of urine. A combination of these two effects will favor presence of higher harmonics as compared to the presence of the fundamental frequency in the return signal. With this information urine quantity or a critical urine filling level of the bladder can be established.

In a third version a combination of a narrow ultrasound beam for detection of the posterior bladder wall distance W with the wide acoustic beam approach for subsequent measurement of urine filling of the bladder is described.

BACKGROUND OF THE INVENTION

It is well known that bladder dysfunction is associated with a number of clinical conditions requiring treatment. In many of these cases it is important to accurately determine the volume of the bladder. Under other conditions such as post-operative recovery, where there is temporary loss of bladder sensation and/or loss of the normal voiding mechanism too much distention of the bladder has to be avoided. Under those conditions voiding by catheter introduction is carried out. However, serious disadvantages to unnecessary catheterization range from the uncomfortable situation for the patient to serious possibilities of infection. Thus, a non-invasive quick measurement of bladder volume, with the patient usually in the supine position, is indicated. Sometimes the accurate determination of volume is indicated; sometimes however an indication is sufficient. Questions that may be asked are for instance: after voiding: "is there still too much urine left?"; or after surgery "is the bladder filling above a certain level so that voiding is necessary?"

Non-invasive procedures for bladder volume estimation are known, but are either unreliable or expensive or have some other significant disadvantages. Palpation and auscultatory percussion are known to be unreliable, while radiography and dye-excretion techniques are known to be similarly inaccurate. For assessing bladder volume, catheterization remains the "gold standard". However, it is invasive, painful and might produce traumas or infections.

Subject

The described technique concerns measurement of urine volume in the human bladder with the use of pulsed ultrasound with a limited number of ultrasound transducers.

In a first version a limited number of transducers are mounted in a transducer assembly. The assembly is positioned non-invasively at the body skin over the position of the bladder with the patient in a supine position. For acoustic contact a coupling gel may be used. Each ultrasound transducer in the assembly transmits and receives the ultrasound signal in a narrow beam through the contact plane. During the measurement the transducers are used in a certain succession. All transducers have been mounted in the assembly such that in transmission and reception successively the beams penetrate the area of the bladder in approximately the sagittal cross sectional plane. The sagittal plane is here defined as ANTERO-POSTERIOR plane of the body. One transducer beam direction is dorsal with in addition at least one transducer beam in the dorsal-caudal and one transducer beam in the dorsal-cranial direction. The volume is calculated on the basis of two bladder measurements defined in the sagittal plane as Depth (D) and Height (H). These measurements are derived on the basis of echo travel time from echoes originating at the anterior and posterior bladder wall. Depth is in principle a measurement in dorsal direction. Height is a measurement approximately in the cranial direction. The volume is calculated depending on the specific, filling dependent, measurement configuration following the formula D×H×K. Where K is an empirically measured, filling configuration dependant, correction factor. Beam directions and examples for D and H are illustrated in FIGS. 1 and 2.

In a second version of the described technique a single wide beam ultrasound transducer is positioned non-invasively at the body skin over the location of the bladder. The wide beam can be created by the curved surface of the transducer or by a flat acoustically active surface of for instance a disk shaped transducer supplied with a curved lens. Ultrasonic signals are transmitted and received in the wide, cone like, ultrasound beam and propagation is approximately spherical. Similar to the above described method a pulsed echo signal is transmitted at fundamental ultrasonic frequency. In this second version of the described technique echo data are analyzed as originating from a distance beyond the average position of the posterior (filled) bladder wall. The received echo signal will contain information over almost the entire bladder as encompassed by the wide ultrasound beam. Due to non-linearity, higher harmonic components will build up during propagation and thus be reflected in the returning echo.

Compared to propagation through normal tissue, the presence of higher harmonics in the signal is greatly stimulated when propagating through urine. Analyses of presence of higher harmonic components in relation to the fundamental frequency is used for indication of presence of urine in the bladder. Neutralizing patient variation as to obesity etc can also be accomplished by comparing echo signals received from sequentially transmitted pulses at low transmit power (linear propagation only) and pulse transmission at high power (enhancing non-linearity).

State of the Art

Non-invasive bladder volume measurement techniques with ultrasound echography have been described in the art. In principle, echography measures distance based on echo travel time. Early echo techniques did use a single ultrasound transducer and echo presentation was recorded as echo amplitude versus depth. West, K A., "Sonocystography: A method for measuring residual urine," Scand J Urol Nephrol 1: pp 68-70, 1967 describes the subsequent use of some discrete beam directions. He does not have a separate transducer for each beam direction. His method is only qualitative, not instantaneous, and based on distance measurement to the dorsal posterior bladder wall. His method is not adjusted to specific, filling dependent, measuring configurations. A relation between the difference in echo travel time between echoes from the posterior an anterior bladder wall and the independently measured bladder volume has been reported by Holmes, J H: "Ultrasonic studies of the bladder", J. Urology, Vol 97, pp. 654-663. His described volume measurement method is exclusively based on bladder depth measurement. Since the bladder changes in shape when filling, a single distance measurement is not precise enough to predict the entire bladder volume. No filling dependent measurement configuration is used.

Diagnostic ultrasound is today well known for real-time cross-sectional imaging of human organs. For cross-sectional imaging the sound beam has to be swept electronically or mechanically through the cross section to be imaged. Echoes are presented as intensity modulated dot on the display. The instruments are costly and require a skilled operator. Volume is sometimes calculated based on bladder contours obtained in two orthogonal planes with a geometric assumption of bladder shape. For 3-dimensional or volumetric echography the sound beam has to be swept through the entire organ. This further increases complexity, acquisition time of the data, and costs of the instrument.

HAKENBERG ET AL "THE ESTIMATION OF BLADDER VOLUME BY SONOCYSTOGRAPHY", J Urol, Vol 130, pp 249-251, have reported a simple method that is based on measuring the diameters obtained in a cross sectional image in the midline sagittal bladder plane only. The bladder volume has been related to bladder Height and Depth as follows: Volume is Height×Depth×6.6 ml. This formula showed a good correlation coefficient (r=0.942) with a relatively large average error of 30.1%. For this approach a two-dimensional imaging apparatus was required. The used apparatus is complex and is different from the method described in this application. It does not use a single wide beam transducer or a limited number of fixed transducers in an assembly or a combination of this.

An ultrasound apparatus for determining the bladder volume is shown in U.S. Pat. No. 4,926,871 in the name of Dipankar Ganguly et al. In this text, a number of possibilities are mentioned, amongst which a scan head embodiment referred to as a sparse linear array with transducers mounted at predetermined angles with sound beams pointing towards the same position. The volume is calculated according to a geometric model. In the claims an apparatus is described, involving an automatic calculation of bladder volume from ultrasound measurements in a first and second plane, which are substantially orthogonal to each other. Sound beams are deflected by a stepper motor. It requires a skilled operator to manipulate the scan head in a particular way to obtain the ultrasound measurements. For the volume calculation method described in this application no use is made of any geometrical model of the bladder, whereas only a limited number of sound beams approximately in the sagittal plane, or a single wide beam is used.

Volume measurement based on echographic sampling of the bladder with a hand guided transducer mounted in a panthograph has been described by Kruczkowski et al: "A non-invasive ultrasonic system to determine residual bladder volume", IEEE Eng in Medicine & Biology Soc 10TH Ann Conf, pp 1623-1624. The sampling covers the entire bladder, follows a given pattern and is not limited to a single or two cross sections of the bladder. For the calculation he needs data from many beam directions. The acquisition procedure is time consuming and thus no instantaneous volume measurement results. The method described in this application is based on use of a single, wide beam or the use of a limited number of mutually fixed sound beams directions with instantaneous volume indication.

The hand steered transducer guiding for recording of echo data from the bladder has subsequently gained in acquisition speed by introduction of constructions whereby the transducer, and thus the beam, was mechanically swept. This nevertheless still requires an acquisition time equivalent to full acquisition procedure and thus does not yield an instantaneous display of volume. No instantaneous feedback on optimal positioning is thus available. An example of such methods is the BLADDERSCAN. In the Bladderscan Technology (registered trademark of Diagnostic Ultrasound Corporation) bladder volume is measured by interrogating a three-dimensional region containing the bladder and then performing image detection on the ultrasound signals returned from the region insonated. The three dimensional scan is achieved by performing twelve planar scans rotated by mechanically sweeping a transducer through a 97 degree arc in steps of 1.9 degrees. The three dimensional scanning requirement makes this instrument complex. It can not be compared with the simple approach described in this application.

Yet another ultrasound method "System for estimating bladder volume" is described by Ganguly et al in U.S. Pat. No. 5,964,710 dated Oct. 12, 1999. This method is based on bladder wall contour detection with echographically obtained data in a plurality of planes which subdivide the bladder. In each single plane of the plurality of planes a number of N transducers are positioned on a line to produce N ultrasound beams to measure at N positions the distance from front to back wall in the selected plan. From this the surface is derived. This procedure is repeated in the other planes as well. The volume is calculated from the weighted sum of the plurality of planes. In Ganguly's method the entire border of the bladder is echographically sampled in 3 dimensions. His method differs strongly from the method described in this application whereby only a single wide beam is used or a limited number of mutually fixed sound directions are used in approximately a sagittal plane with a filling dependent measurement configuration.

U.S. Pat. No. 6,359,190 describes a device for measuring the volume of a body cavity, such as a bladder or rectum, using ultrasound. The device is strapped to the body or incorporated into a garment such as a nappy or trainer pant. The device includes several transducers each aimed at a different region of the subject's bladder (a) to ensure that at least one ultrasound beam crosses the bladder despite variations in the way that the device has been positioned on the body, and (b) to enable the transducer with the strongest signal output to be used. An alarm signal may be output when the bladder reaches a predetermined threshold volume.

An important parameter for assessing bladder volume if this volume has to be derived from a limited number of beams or planes is the knowledge of bladder shape and position which can drastically vary with age, gender, filling degree and disease. In the adult patient the empty bladder has the shape of a triangular prism and is located behind the pubis. When it is progressively filled, there is first a distention of the bladder depth followed by an expansion of the bladder height. The bladder shape is complex and can not be represented by a single geometrical formula such as ellipsoid, sphere etc. This explains the large error that several studies obtained when a single geometric model was used. However there exists a correlation between the bladder height and the bladder widening with progressive filling.

In the first approach of the present invention an instrument is described which allows assessment of bladder volume by using only a few ultrasound beams appropriately oriented in approximately the sagittal plane. The narrow sound beams in principle diverge relative to each other. This allows covering a wide range of filling degrees of the bladder, from almost empty, when the bladder is located behind the pubis, to a full bladder that causes a substantial bladder height (See FIGS. 1 and 2). From each beam can be established, by detection of the posterior bladder wall echo, if this beam does pass a filled bladder. From the knowledge of all beams that do pass the filled bladder the appropriate filling or measurement configuration follows. The acoustic beams are positioned in such a way that the Depth D and Height H of the bladder can be estimated for the specific measurement configuration. The volume of urine is then computed from an empirical formula D×H×K that does not depend on any geometric model. K is a known, empirically established correction factor which is specific for each measurement configuration and has been established by calibrated bladder measurements on a prior series of patients. The accuracy of the first approach is thus based on an a prior known correction factor which is related to a specific filling degree, which in turn depends on the number of beams that intercept the filled bladder.

A second version of the instrument is based on the measurement of the presence of higher harmonics in the echo signal. For this approach the echo signal from a depth greater than the distance from the transducer to the posterior bladder wall must be analyzed. For a filled bladder in adults in a supine position, this depth W would be approximately 12 cm.

It is known that when sound pulses are transmitted at a fundamental frequency, higher harmonics of this fundamental frequency may be present in the received echographic signal. Non-linear distortion increases with distance, insonifying ultrasound energy and frequency. Attenuation diminishes the ultrasound amplitude with increasing propagation distance and reduces the higher harmonic energy. Since attenuation of the ultrasound signal in urine is low compared to tissue and non-linear distortion in urine is large compared to tissue it results that urine is very different from tissue in its ability to generate higher harmonics. We have measured the presence of higher harmonics in the echo signal from 12 cm depth when the bladder was filled. With an empty bladder the echoes obtained from the same depth did not contain higher harmonics.

The interest of higher harmonic signals in the ultrasound technique stems from echo contrast technology. Echo contrast material contains coated gas containing micro bubbles suspended in a fluid. These bubbles can create higher harmonic components in the echo signal due to non-linearity. This is used to indicate presence of contrast on the diagnostic image. A wide variety of pulse techniques is used to stimulate echographic visibility of contrast. These include multi pulse procedures, multi frequency procedures, power Doppler imaging, pulse coding, pulse inversion and other imaging methods. A survey is documented in "Ultrasound Contrast Agents" ISBN 1-85317-858-4 chapter 3 "Contrast-specific imaging methods" by de Jong et al. With a single transducer with wide sound beam, such as results with a curved acoustic element or a flat, disk shaped transducer plus curved lens, the propagating sound beam would encompass the entire bladder. The transducer must be designed to optimally transmit the fundamental ultrasound frequency and at the same time be capable to receive fundamental and higher harmonic echo signals. Broadband piezo-electric ceramic transducers have been described as well as combination transducers using ceramic in transmission and PVDF material in reception. In transmission a single or multi pulse procedure can be followed. If the returned echo signal with such a method would, in relation to the fundamental echo signal, be analyzed for the presence of higher harmonics, the presence of a certain level of bladder filling or the volume of urine can be established.

EP 0271214 describes an ultrasonic device for monitoring the volume of fluid in the human bladder by using reflected ultrasound signals to determine not only the position of the bladder back wall but also energy returned from the bladder back wall. EP '214 proposes that after bladder filling to approximately 60% capacity, the distance between the back wall and the front wall of the bladder stops increasing. However, additional reverberation in the back wall provides an increase in energy in the reflected signal which can be used to determine further increases in bladder volume.

DESCRIPTION OF THE DRAWINGS

In FIG. 1 the patient's leg is indicated by 4.

DETAILED DESCRIPTION OF THE FIRST METHOD

The first method describes a simple device that allows the assessment of bladder 23 volume, using only a few beams appropriately oriented. Under the assumption that there exists a correlation between the bladder height and width, a simple approach has been developed. It consists of a limited number of acoustic beams positioned in such a way that the depth D and the height H of the bladder could be estimated in approximately a single sagittal plane. The volume of urine is then computed from an empirical formula that does not assume any geometric model.

Figure 5:
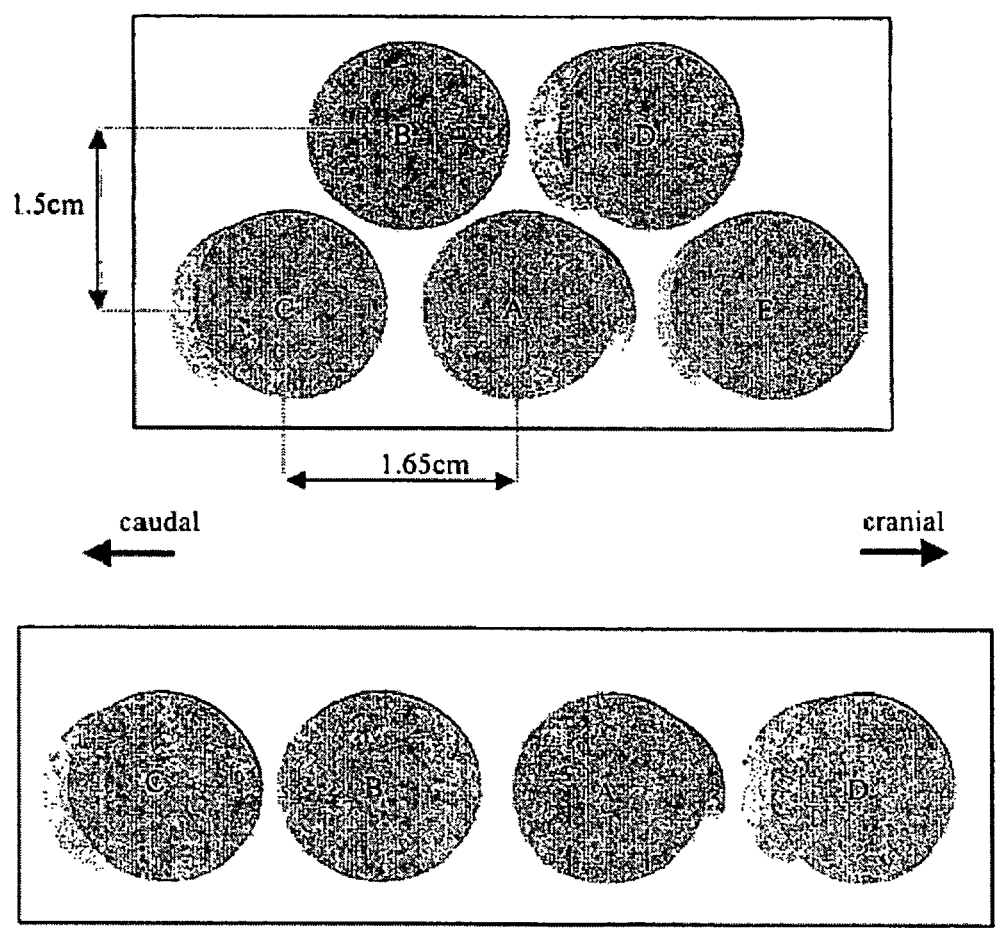
FIG. 5. Illustrates a top view of five disk shaped transducers in a possible transducer assembly. The distance between transducers B, D and C, A, E and their positioning is such that all sound beams can be assumed to be in approximately a sagittal cross section through the bladder. Yet another transducer assembly with 4 transducers in a row is also illustrated.
Figure 6:
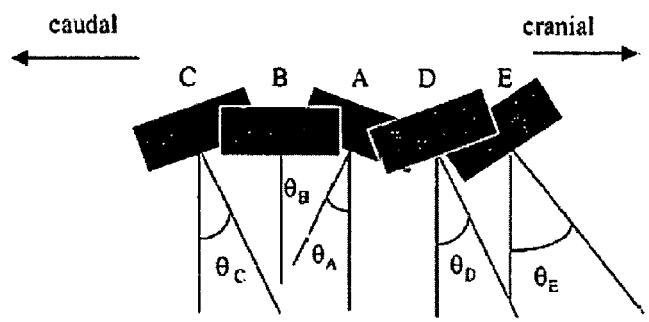
FIG. 6. Illustrates a cross sectional view showing in the length direction a possible transducer and related sound beam orientation when five single transducers are used.

In operation of the apparatus of the present invention, the transducer assembly 1 is placed on the abdomen of the patient in the supine position, just above the symphysis pubis 2. We are presenting a particular configuration of the assembly 1. Nevertheless, various configurations can be derived from this model and several modifications could be achieved (number of transducers, position, orientation, etc. . . . ) without departing from the initial ideas. The device proposed as an example is composed of five disc shaped transducers A, B, C, D and E (focused or non-focused) positioned in the assembly at predetermined distance from each other (FIG. 5, top panel) and oriented at predetermined angles $Ø_A$, $Ø_B$, $Ø_C$, $Ø_D$, and $Ø_E$ (FIG. 6). Referring to FIG. 5 (top panel), it appears that the transducers A, B, C, D and E are oriented in two different planes. The distance between these two planes is small compared to the bladder 3 size and thus we can assume that the information received from each transducer represent the characteristics of approximately a single sagittal or anteroposterior plane. The orientation of each beam has been determined from the knowledge of the bladder 3 position and shape when it is filling up as measured in a patient series. The first beam of the transducer assembly 1 (soundbeam from transducer A) is oriented in such a way that it reaches the bottom of the bladder, passing just above the symphysis pubis 2. The remaining beams are positioned for successively intercepting the bladder 3 when it expands with increasing filling degree.

Computation of the Depth D and Height 5: Depending on the number of beams that are intercepting the bladder 3 and on the geometrical configuration of the transducer assembly (1), the distances H and D are determined by different mathematical procedures. For most measurement configurations the depth D of the bladder is determined by the distance between echoes derived from front and back wall of the bladder estimated from Transducer B.

Figure 1:
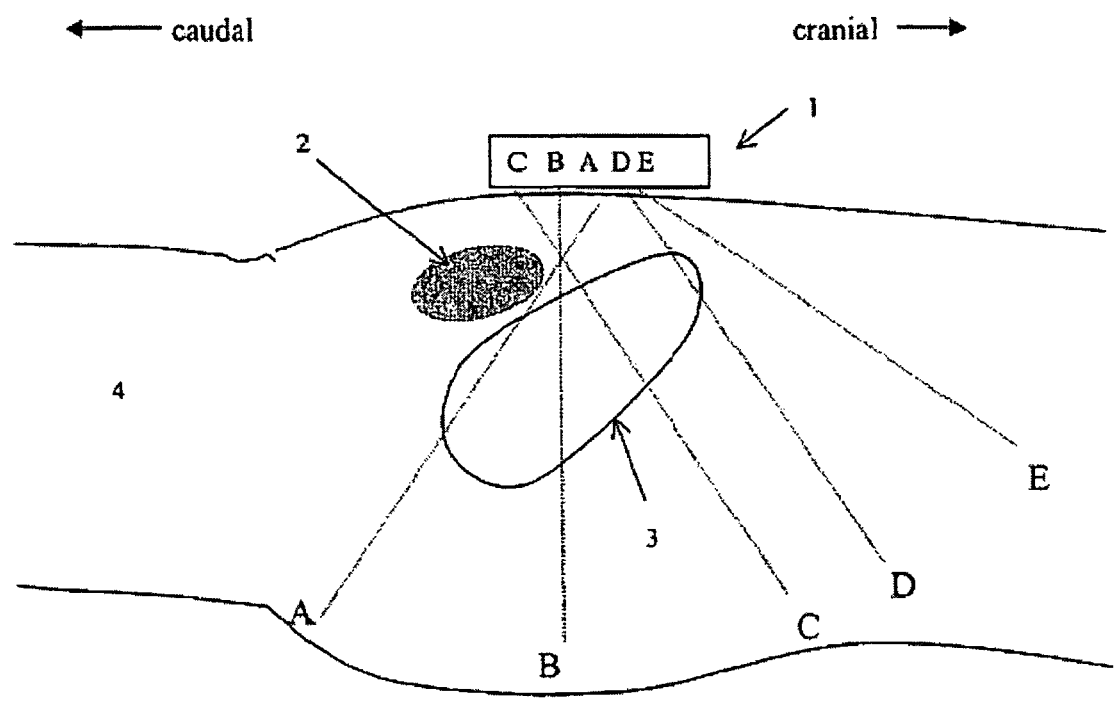
FIG. 1 Illustrates a sagittal (anteroposterior) cross sectional plane of a patient in supine position where a transducer assembly 1 with transducers A, B, C, D and E, is positioned on the abdominal wall just above the Symphysis Pubis 2 and the ultrasound beams are indicated to cross the area of the partially filled bladder 3. From the transducer assembly, the sound beam A intercepts the bladder area in dorso-caudal direction, soundbeam B intercepts the bladder in dorsal direction and sound beams C, D, and E respectively in dorso-cranial direction.
Figure 2:
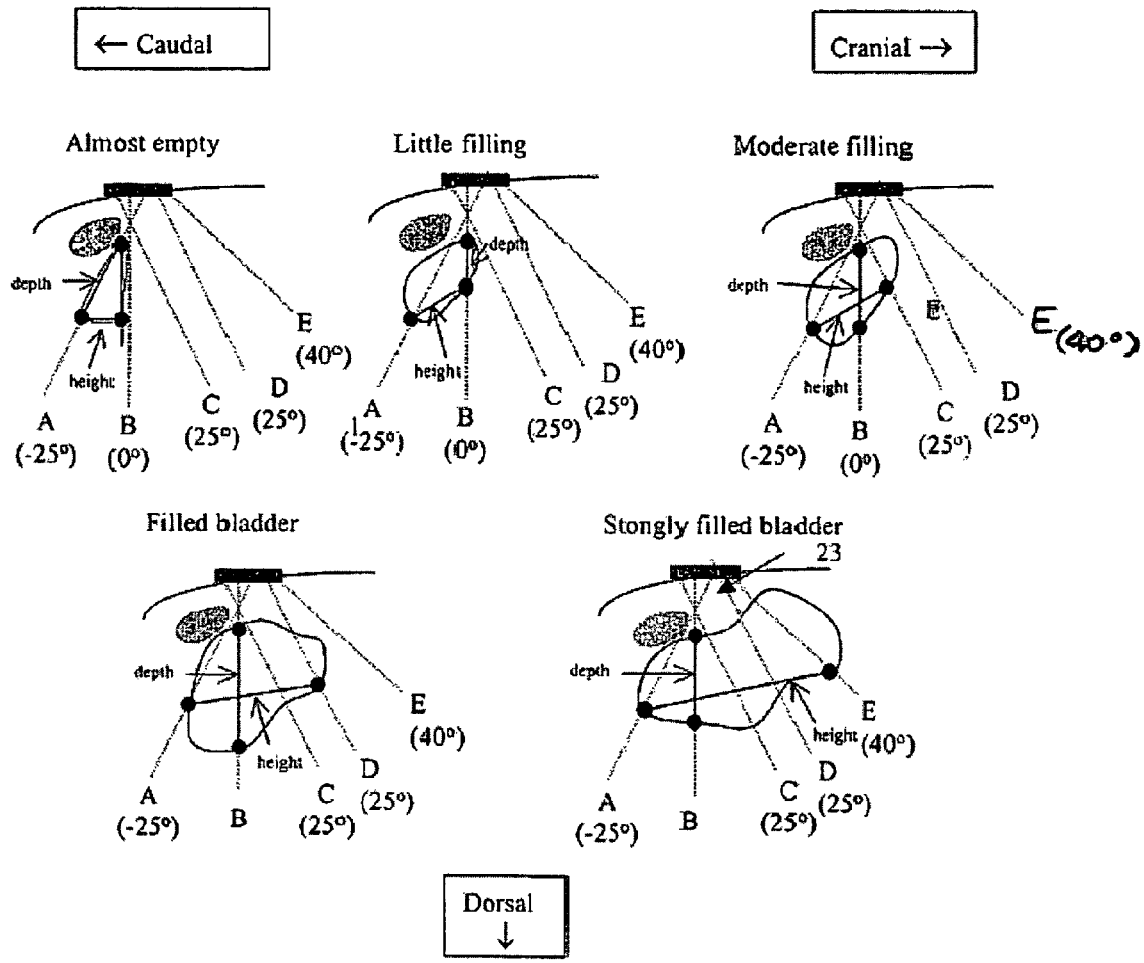
FIG. 2 Illustrates various bladder filling stages from an almost empty bladder to a strongly filled bladder and the corresponding measurement configurations. Depth D and Height H have been defined for each filling situation as indicated and are calculated from detected bladder wall echoes taking the specific measurement configuration into account. For each measurement configuration a specific Depth D and Height H is defined.
Figure 3:
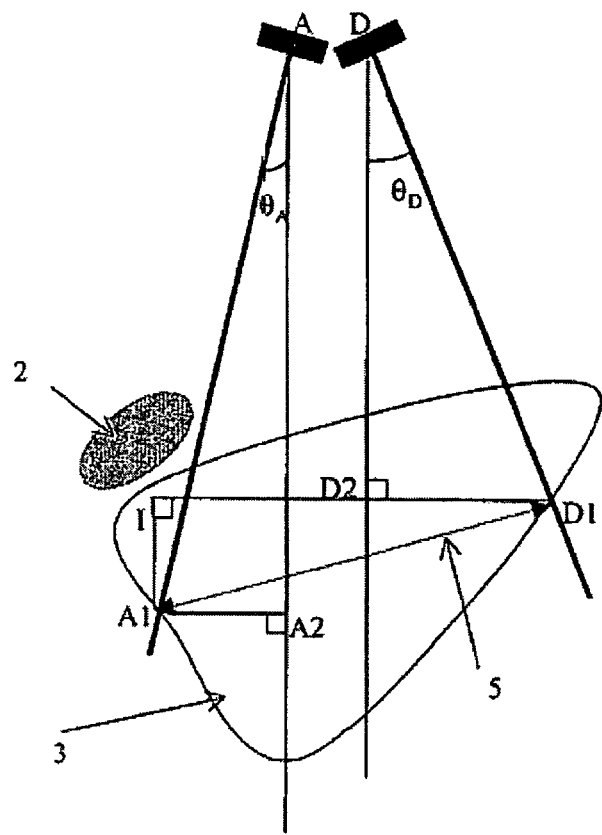
FIG. 3. Illustrates, by way of example for a transducer assembly with five transducers (here only A and D, necessary for calculation of H are shown), the calculation of Height H (5) in the measurement configuration when bladder posterior wall echoes are detected originating from sound beam A, B, C and D. This is the "filled bladder" measurement configuration shown in FIG. 2. Apparently no posterior wall echoes are detected in sound beam E because the bladder filling is not yet in a strongly filled stage and thus beam E does not intercept the bladder. Depth D is derived from beam B (not shown in FIG. 3).

The Height H (5) calculation in the specific measurement configuration (here we selected as an example the "filled bladder" configuration of FIG. 2) when posterior bladder wall echoes are detected in signals obtained in beam A, B, C, and D, but not in beam E is illustrated in FIG. 3. For the other filling geometries the height is calculated in a corresponding way. The mathematical procedure is as follows:

$$\cos Ø_A = [AA2]/[AA1] => [AA2] = \cos Ø_A \cdot [AA1] \quad (1)$$

$$\sin Ø_A = [A1A2]/[AA1] => [A1A2] = \sin Ø_A \cdot [AA1] \quad (2)$$

$$\cos Ø_D = [DD2]/[DD1] => [DD2] = \cos Ø_D \cdot [DD1] \quad (3)$$

$$\cos Ø_A = [D1D2]/[DD1] => [D1D2] = \sin Ø_D \cdot [DD1] \quad (4)$$

$$\cos Ø_A{}'' = [AA2]/[AA1] => [AA2] = \cos Ø_A \cdot [AA1] \quad (5)$$

$$\cos Ø_A{}'' = [AA2]/[AA1] => [AA2] = \cos Ø_A \cdot [AA1] \quad (5)$$

$$ID1 = [D1D2] + [A1A2] + [AD] \quad (6)$$

$$=> \text{Height} = [A1D1] = \sqrt{[A1I]^2 + [ID1]^2} \quad (7)$$

Volume computation: The volume of urine is correlated to the bladder diameter (Height 27 and Depth 26) by the empirical formulae:

Height*Depth*K where K is a correction factor. Depending on the number of beams that allow the determination of the bladder dimensions (from 1 to 5) and others parameters such as the age, the gender, the correction factor is different. For a given situation (parameters other than number of beam are fixed), the correction factors KL, K2, K3, K4 and K5 are optimized using linear regression analysis.

Figure 4:
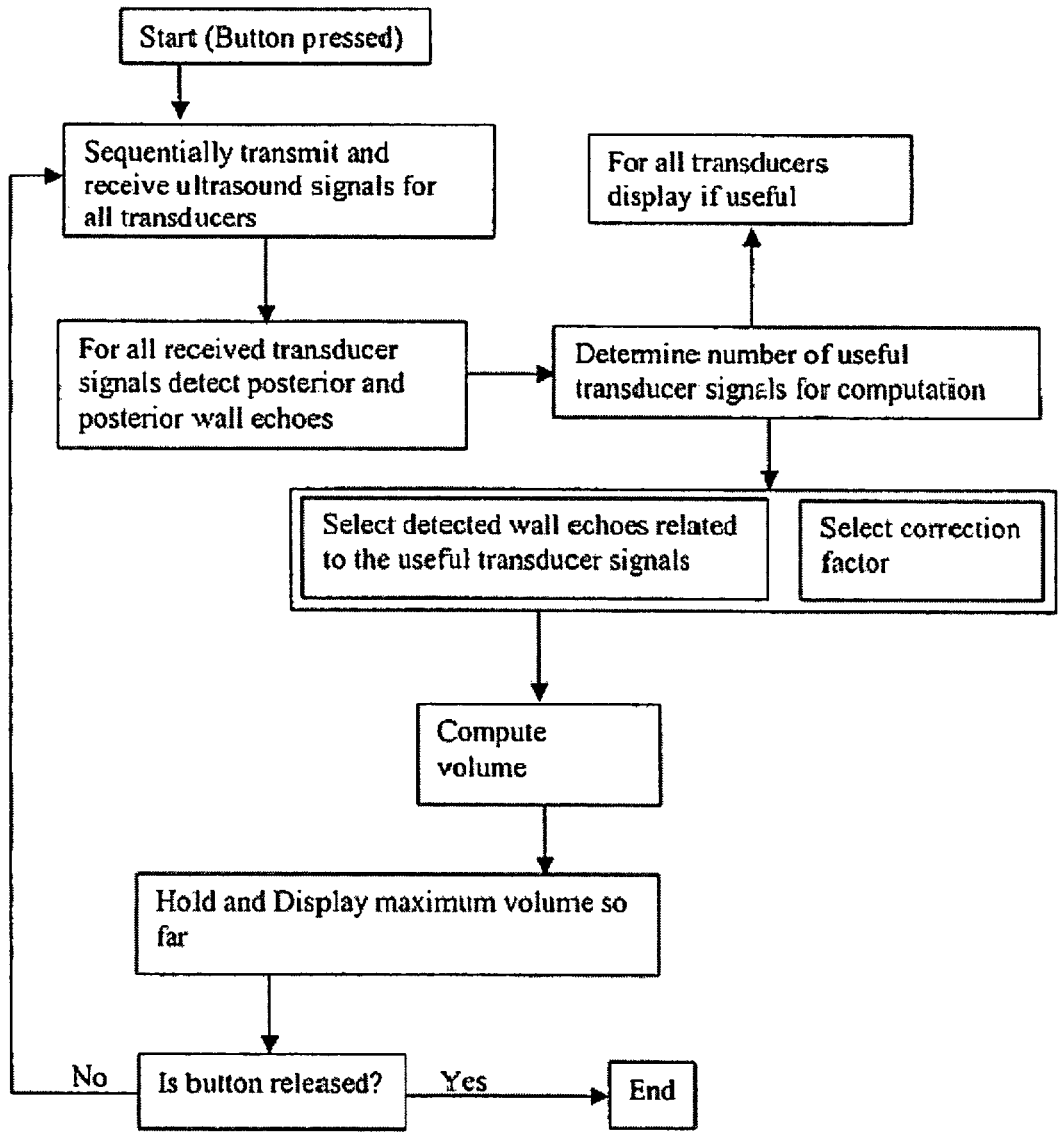
FIG. 4 Represents a flow chart of the actions of the principal hardware components. In this block diagram a "useful" transducer signal occurs when bladder wall echoes are detectable in its sound beam.

The process executed by the hardware is illustrated in the flow chart of FIG. 4.

After positioning the transducer assembly correctly over the bladder area the measurement procedure is started by pressing the start button which during the (short) measurement procedure remains depressed. Subsequently the transducers are activated for transmission of ultrasound pulses and reception of echoes and possible detection of bladder wall echoes in a specific order. Thereafter it is established, when a clear posterior bladder wall echo is detected, which ultrasound beams, this we call here the beams of "useful" transducers, penetrate the filled bladder. From this, the filling situation or measurement geometry is established. As a result the proper correction factor can be selected. After calculation of the volume the value is stored in memory and displayed. During the measurement procedure the transducer assembly is slightly moved and memory data are refreshed if a larger volume is measured. The highest value will correspond with the correct bladder volume. This is displayed.

In a general aspect, therefore, the apparatus may use beam information comprising at least: angle of incidence (known from the transducer mounting angle), spatial position (known from the transducer position in the array) and echo travel time (deduced from the reflected beam). Other beam parameters or information from reflected beams may also be used in accordance with known ultrasound techniques, such as frequency, pulse rate etc.

For determining body cavity and height, the apparatus may select only beams corresponding to those that have intercepted the fluid filled body cavity.

The arrangements described in connection with FIGS. 1 to 6 illustrate use of five transducers. This configuration was selected in order to achieve a selected degree of accuracy of measurement over a complete expected range of total volumes in a human adult. In the preferred configuration, accuracy of measurement of the order of 100 ml over a range encompassing a bladder fill level from 0 to approximately 800 ml has been exhibited. It will be understood that a smaller number of transducers could be used when either the desired measurement accuracy can be reduced, or when the total fill range covered can be reduced.

For example, using just three transducers, it has been shown to be possible to cover a fill range of 0 to approximately 500 ml with an accuracy of 100 ml.

Similarly, four transducers has been shown to cover a range 0 to approximately 700 ml, and two transducers, a range of 0 to approximately 300 ml.

Such configurations can be used when it is only necessary to indicate gross ranges of bladder filling, or to indicate a clinically important threshold fill level.

In other embodiments, the apparatus may be provided with an input device such as a keypad or computer interface so that the user can enter patient information, such as gender, weight and age. This information can then be used to ensure correct selection of an available correction factor, K, from a memory of the apparatus.

The apparatus may also be provided with means for inputting calibration data, such as absolute measurements of bladder fill level separately deduced from conventional measurements. These can be stored by the apparatus and used to optimise stored K values as part of an iterative, 'self-learning' process. In other words, the apparatus may incorporate an algorithm for automatically adjusting predetermined correction factors stored therein based on calibration data entered into the machine for comparison with measurement data taken by the apparatus.

The apparatus may also comprise a means for indicating correct caudal-cranial positioning of the transducer array on the body over the bladder. For example, in a normal measurement as suggested in figure, it is expected that at least transducers A, B and C will indicate a bladder present condition, whereas transducers D and E might, or might not indicate bladder present, according to the bladder fill level. In the event that, for example, no signal is indicated by A, or by A and B, but signal is indicated by D or D and E, then it can be deduced that the transducer assembly is positioned too far in the cranial direction. This could be indicated on the display of the device.

In summary, the described first method differs greatly from known other apparatus:

1) The device is composed of a limited number of static single element transducers;

2) The arrangement of the transducer is not similar to the arrangement of a linear array;

3) The transducers are oriented towards the bladder with specific angles allowing the estimation of the urine volume over a wide range of volumes;

4) The method for automatic volume computation does not assume any geometrical model for the bladder shape;

5) It is valid for any bladder shape since the volume is computed with an empirical formula for various filling ranges;

6) It is not based only on the measurement of distances between the front and back wall or area in different planes;

7) It uses an automatic detection of the bladder height and depth depending on the number of beams that intercept the bladder;

8) It optimizes the correction factor depending on the degree of filling (or other factors, such as age, gender, weight, that may influence the calculations);

9) The device includes a closed loop to easily find the optimal position;

10) The optimal position corresponds to the largest volume computed;

11) The device works instantaneously.

DETAILED DESCRIPTION OF THE SECOND METHOD

The second version of the device is based on a different principle. The approach consists of using a single acoustic beam with a very wide width such that it encloses approximately the entire volume of the bladder when it is filled up. Such a wide beam width can be obtained using a single element transducer with a defocusing lens as drawn in FIG. 7 or a curved single element transducer.

Figure 7:
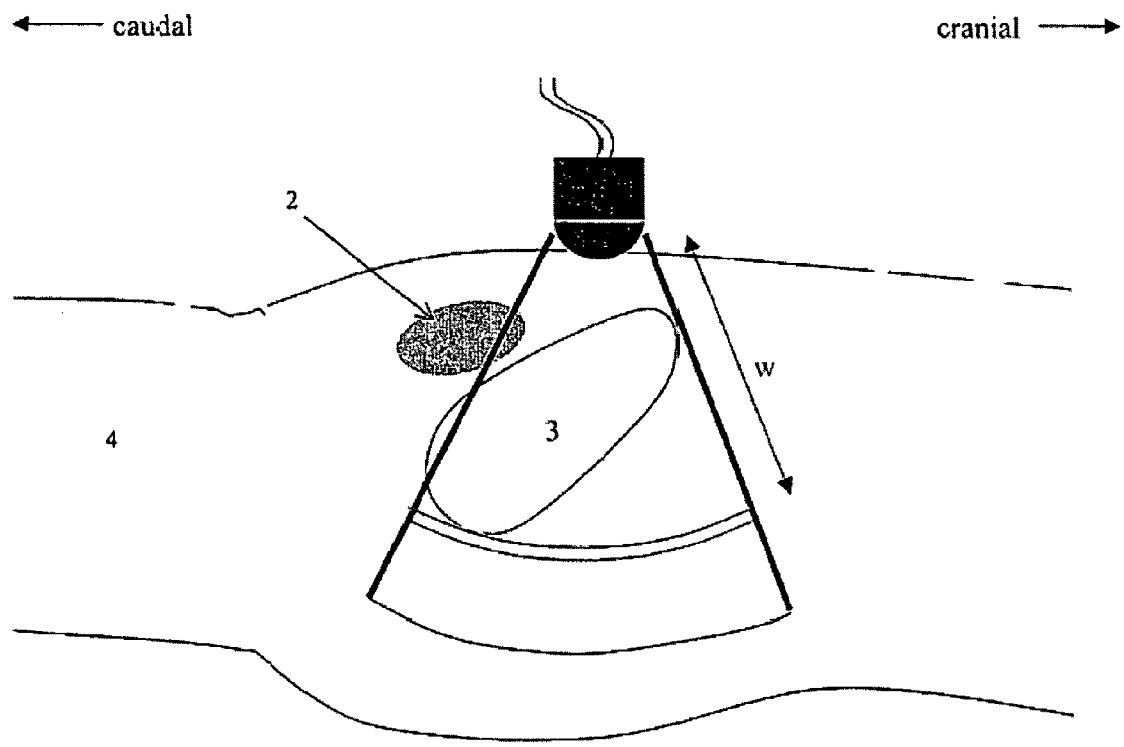
FIG. 7 Illustrates the sagittal cross sectional plane with a single wide beam transducer non-invasively positioned on the abdominal skin surface over the filled bladder 3. Echo signal is received from a range at depth W.

The schematic principle of transducer positioning is illustrated in FIG. 7. The sagittal cross section through the bladder is shown. The cone like shape of the acoustic beam allows to encompass approximately the full bladder volume, and therefore any harmonic distortion detected in the echo signal returning from a region beyond the posterior wall of the bladder around depth W, would correlate to the amount of fluid contained in the bladder.

It has been demonstrated that the propagation of ultrasound waves is a nonlinear process. The nonlinear effects, which increase with higher intensities, have been predicted and demonstrated at frequencies and intensities used in the diagnostic range either in water or in human body (A Baker et al.: "Distortion and High-Frequency Generation Due to Non-Linear Propagation of Short Ultrasonic Pulses From A Plane Circular Piston", J. Acoustic Soc Am 92(3), pp 1699-1705). The distortion is due to slight non-linearities in sound propagation that gradually deform the shape of the propagating sound wave, and result in development of harmonic frequencies which were not present in the transmitted wave close to the transducer. This manifests itself in the frequency domain as the appearance of additional harmonic signals at integer multiples of the original frequency.

These effects occur most strongly when ultrasound waves propagate within liquids with relatively low acoustic attenuation such as water, amniotic fluid or urine. Indeed, acoustic propagation in fluids gives rise to extreme nonlinear effects at diagnostic frequencies. Within soft tissues, nonlinear processes also take place but are modified as a result of the different acoustic characteristics of these tissues, most notably their high acoustic absorption. Indeed, water and amniotic fluids (urine) are significantly different from tissue.

It is known from literature (A C Baker: "Prediction Of Non-Linear Propagation In Water Due To Diagnostic Medical Ultrasound Equipment", Phys Med Biol 1991 VOL 36, NO 11, PP 1457-1464; T Szabo et al.: "Effects of Non-Linearity On The Estimation Of In-Situ Values Of Acoustic Output Parameters", J Ultrasound Med 18:33-41, 1999; M Hamilton et al.: "Nonlinear Acoustics", Academic Press) that the non-linearity of a medium is characterized by the coefficient of non-linearity β. Typical values for P are 3.6 for water, 4 for blood and 6.5 for fatty tissue.

In addition to being nonlinear, all the media have acoustical loss due to absorption. The acoustical loss is described by the power law: A=AOFB where ao is constant and b ranges from 1 to 2 depending on the medium. For water, the rate of absorption of an ultrasound wave propagating through it is quadratically related to the frequency (b=2). However, the rate of energy loss due to absorption is considered small and most of the time the dissipation-less theory is applicable over short ranges. However, biological media have large rates of energy loss and the frequency dependence has an exponential value of 1 to 1.5.

By considering both attenuation due to absorption loss and non-linearity, the exchange of energy between the two processes is complicated, because attenuation diminishes the amplitude of the generated harmonic components with propagation distance while non-linearity builds up these harmonics. So, harmonic distortion generally tends to enrich the higher harmonic components at the expense of the lower ones (energy transfer), while absorption damps out the higher components more rapidly than the lower ones. It is therefore difficult to reach a balance in which a given component loses as much energy by absorption as it gains from nonlinear distortion. Moreover, since the conditions for stability depend on the amplitude of the wave, which slowly decreases with propagation distance, the wave can never be completely stable, only relatively so.

The balance between the nonlinear process and the attenuation process is given by the Goldberg number Γ (Szabo et al.), which represents a measure of which process dominates. When Γ=1, nonlinear effects are comparable to attenuation effects. If Γ is higher than 1, nonlinear processes dominate and when the Goldberg number is below 1, attenuation effects take over. As indication, for acoustic pressures of 500 kPa and LMPA, at a transmit frequency of 3 MHz, the Goldberg number is respectively 86.5 and 43.2 for water. It is only 2.8 and 1.4 for liver-like tissue respectively at these pressures. For both settings, the parameter shows that for water, non-linearity is up to thirty times greater than for tissue.

The approach used here is based on the "non-linearity/attenuation" characteristic in differentiating between fluid media and soft tissue media. As described above, a single element transducer is placed in front of the bladder. The transducer generates a wide acoustic beam that is able to enclose the full bladder volume. Depending on the volume of urine contained in the bladder (bladder filling) and thus crossed by the acoustic beam, the amount of harmonic distortion generated in the back of the bladder will change.

A radio frequency (RF) backscattered signal might be selected from a region of interest located preferably in the backside of the bladder. The amount of energy comprised in the second harmonic or higher harmonic components of the received RF echo signal can be extracted and correlated to the amount of volume of urine that has been encompassed by the acoustic beam. Since harmonic generation is different in tissue than in fluids, only the volume of urine that has been crossed by the acoustic beam would generate more harmonic energy. When the bladder is empty or below a certain volume level, no harmonic distortion occurs, whereas maximal distortion will be obtained for a full volume.

Figure 9:
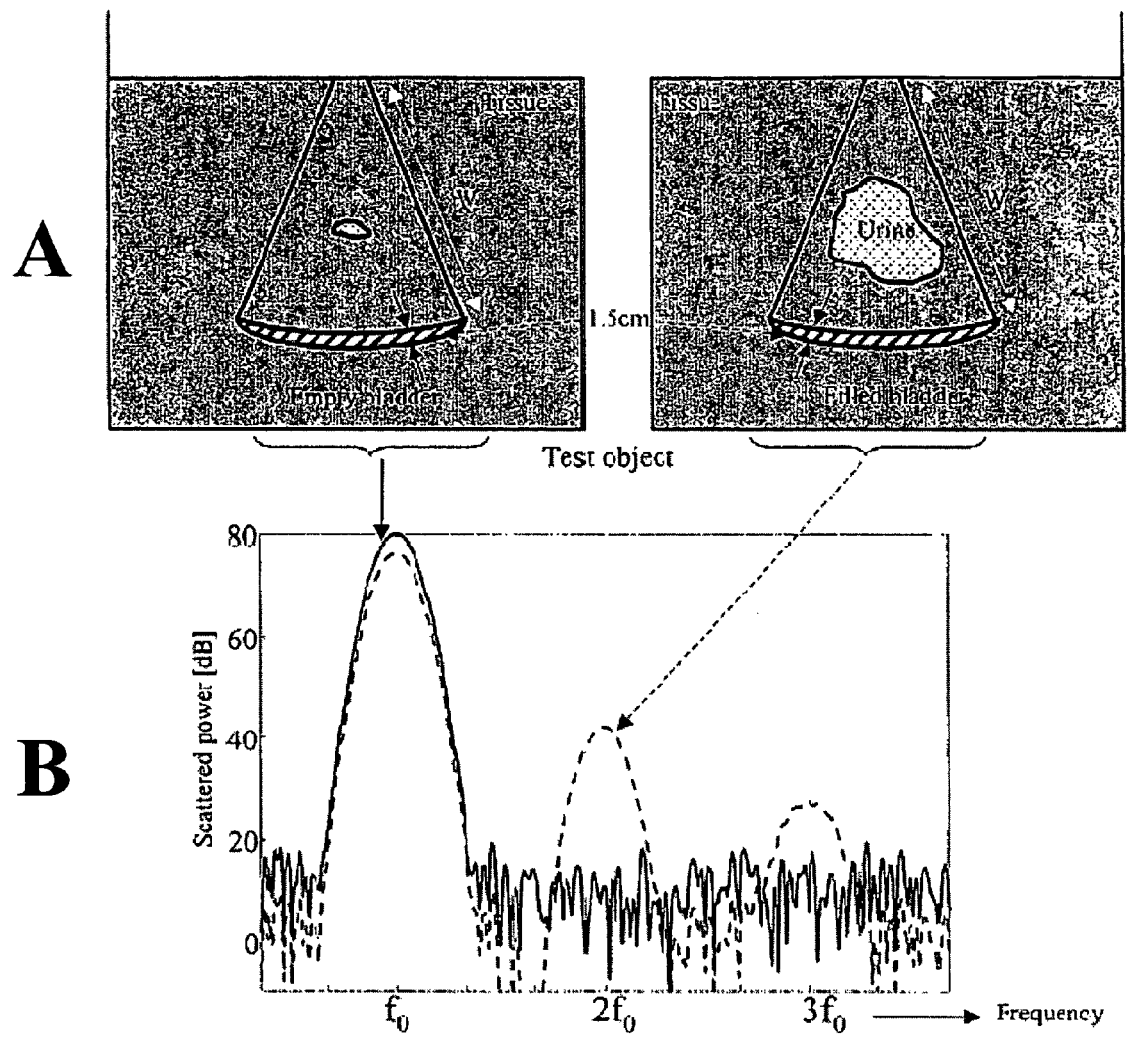
FIG. 9. Illustrates the measured received scattered power in the fundamental frequency to and the higher harmonic frequencies $2f_0$ and $3f_0$ in a situation with an empty versus a filled bladder.

FIG. 9 illustrates the principle of the invention. Top panel shows two situations. The bladder is either empty (Panel A left side) or filled up with urine (Panel A right side). At a certain distance beyond the bladder (around 12 cm from the transducer), a region of interest of 1.5 cm width at depth W (see FIG. 7) is selected. Power spectra corresponding to echo signal recorded from the regions of interest are displayed in panel B.

The spectrum corresponding to the empty bladder (solid line) shows only a fundamental component. The harmonic distortion is very weak so that no harmonic frequencies are generated. However, the echo signal corresponding to the filled bladder situation (dashed line) demonstrates clear distortion where a second harmonic component with a significant energy is generated. The third harmonic component can be also present with lesser energy depending on the urine volume that has been crossed by the acoustic beam.

FIG. 9 demonstrates that depending on the volume contained in the bladder that the acoustic beam has intersected, the amount of generated second harmonic energy varies. When the acoustic beam crosses only tissue or when the volume of urine is very small, harmonic distortion is the lowest with no or very low harmonic energy. If the bladder is filled up or if the volume of urine is above a certain level (threshold), harmonics are generated. The generation of a harmonic component (second and/or higher harmonics) can be used for volume measurement, or simply as an indicator of filling of the bladder to a certain volume extent. The criterion can be such that if a certain amount of second harmonic (or higher harmonics) is generated in the echo signal, the device would indicate that the critical volume (or threshold) (say in adult patients around 450 ml) has been reached.

To avoid and eliminate any differences due to patient to patient variations, a normalization procedure needs to be performed a priori. Such a normalization procedure might consist of recording a first signal at very low transmit acoustic power from the same region of interest as described in the previous section. Such power would allow only linear propagation of the ultrasonic waves and avoid any harmonic generation. The echo signal would therefore have undergone only attenuation effects.

In the following transmit-receive sequence, the transmit acoustic power is increased with a certain factor (e) and a new recording is performed from the same region of interest. This measure with a much higher acoustic pressure is carried out to allow harmonic distortion to occur in the tissue. The echo signal in this case will undergo both attenuation and distortion effects. The first echo signal (linear case) will be re-scaled by the factor that corresponded to the increase in transmit power (e), and then used as a reference signal. Consequently, each patient has his own reference hence eliminating any variations such as obesity, INHOMOGENEITIES, etc.

Figure 8:
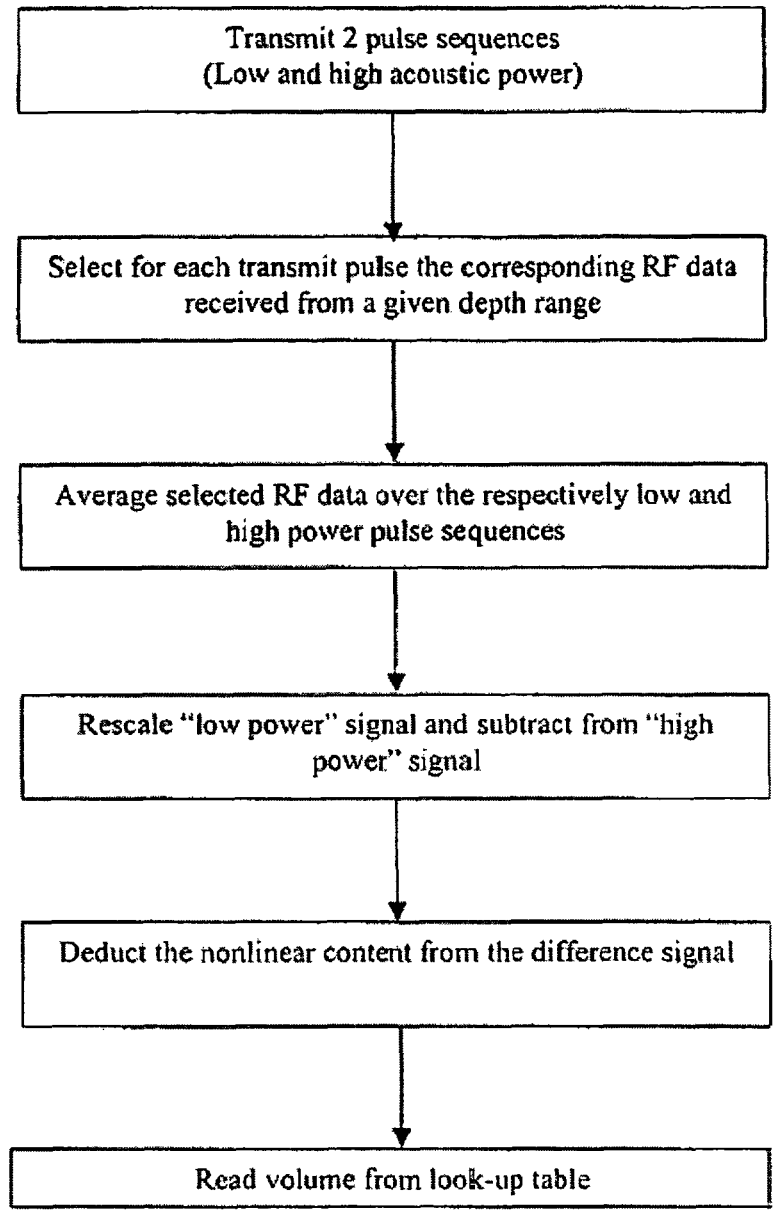
FIG. 8. Is a flow chart illustrating the principal steps taken by the bladder volume measurement instrument based on a single ultrasound wide beam where detection of presence of higher harmonics in the received signal from a give depth range is used to measure volume. Two different transmit levels are used to enhance the bladder effect and eliminate patient variation.
Figure 10:
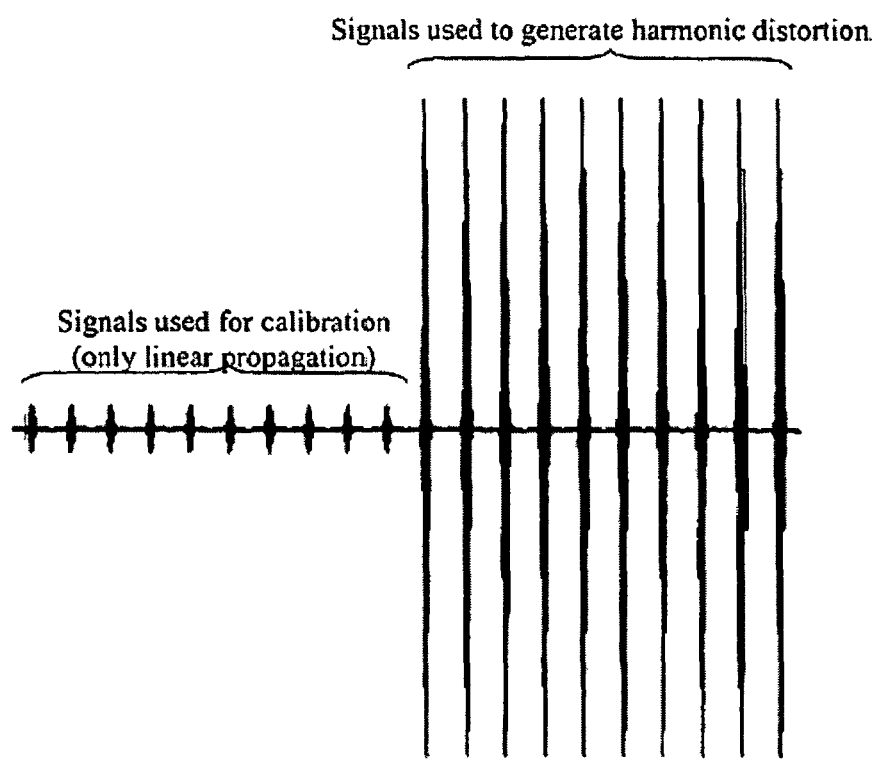
FIG. 10 shows two possible transmit pulse sequences to enhance the difference between linear and non-linear sound propagation.

A block diagram of a possible steps describing the second method is given in the flow chart of FIG. 8. The two transmitted signals might be transmitted with a very low repetition rate as indicated in FIG. 10. The first packet of transmit signals with low acoustic amplitude are used for calibration. The echoes received from those signals are averaged to reduce the noise level.

The number of signals can be chosen such that a high signal-to-noise ratio is obtained. The second packet of signals with higher amplitudes are used to induce nonlinear propagation and harmonic distortion. The echoes received from these signals are averaged and then the harmonic energy is filtered and then compared to the calibration echo.

Figure 11:
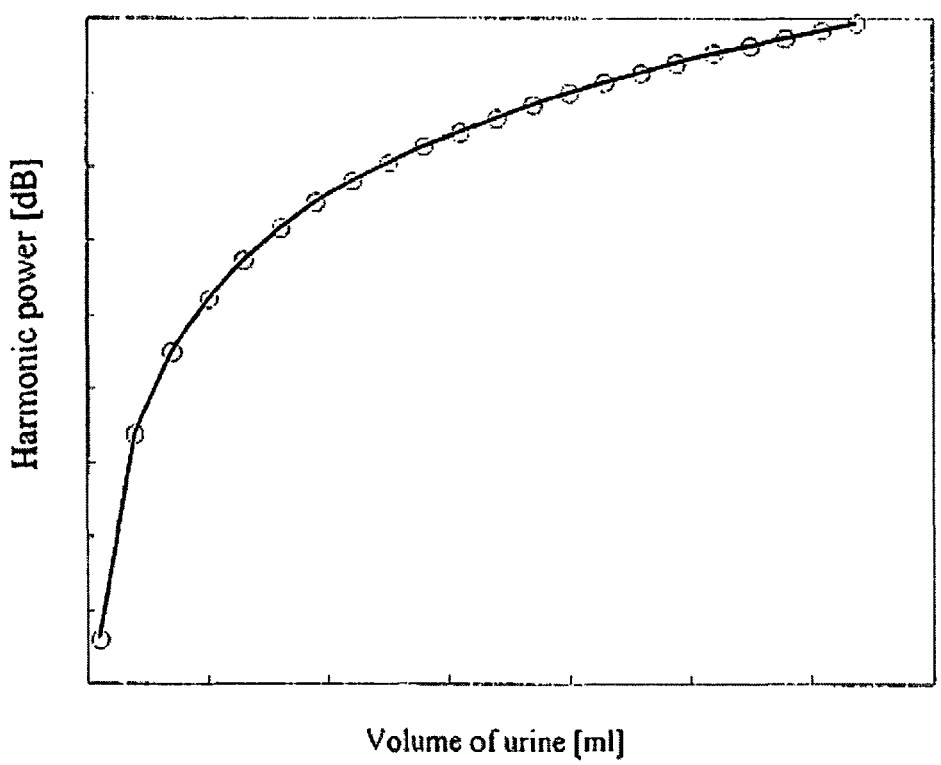
FIG. 11 Illustrates a possible look-up table based on prior calibrated patient bladder volume measurements relating presence of harmonic power in the received echo signal versus volume.

In order to estimate the volume of urine in the bladder, a look-up table can be created beforehand. Such a table, saved in the hard disk of the electronic device, will contain the correspondence between the harmonic energy and the volume of urine. Such a table can be extracted from a curve similar to the one given in FIG. 11. Such a curve can be obtained from a "learning" patient set of measurements. Look-up tables may eventually be produced for specific patient groups for age; gender and/or weight as an input parameter.

The described second method differs greatly from known other apparatus:

12) The device is composed of a single element defocused ultrasound transducer with a conical beam shape;

13) The single acoustic beam entirely encompasses the volumetric area of a possibly filled bladder.

14) The method is based on measurement of non-linear properties and attenuation behavior of propagating ultrasound waves as influenced by a urine filled bladder.

15) The method incorporates a technique to eliminate patient variation due to fat or skin properties.

16) The method for automatic volume computation does not assume any geometrical model for the bladder shape;

17) It is valid for any bladder shape since the received signal "integrates" all volume effects in the ultrasound beam.

18) All known other methods use bladder wall echoes as a basis to calculate volume.

19) The device works instantaneously. Other embodiments are intentionally within the scope of the accompanying claims.

We claim:

1. An apparatus for measuring the volume of fluid in a human or animal body cavity using a non-invasive, ultrasound echo technique, comprising:
   a transducer configured to:
      transmit at least a first ultrasound signal at a first power level into the body such that the at least first ultrasound signal reaches a portion of the body cavity, the body cavity being at least partially empty of the fluid such that the respective volumes of the body cavity and the fluid are different from one another, and
      transmit at least a second ultrasound signal having a first frequency and at a second power level higher than the first power level such that the at least second ultrasound signal reaches the portion of the body cavity;
   a receiver component configured to receive at least a first ultrasound echo signal from the body cavity for the at least first ultrasound signal, and receive at least a second ultrasound echo signal for the at least second ultrasound signal; and
   a processor component configured to:
      determine a reference signal based on the at least first ultrasound signal and the received at least first ultrasound echo signal, wherein the reference signal is used to eliminate effects of variation caused by patient anatomy,
      determine a measure of an energy level of a harmonic component of the received at least second ultrasound echo signal, wherein the harmonic component corresponds to at least a second harmonic having at least two times the first frequency,
      re-scale the reference signal based on an increase in power level between the first power level and the second power level, and
      determine the volume of the fluid in the body cavity based on the measured energy level of the harmonic component and the re-scaled reference signal, wherein determining the volume comprises accessing a table storing correspondences between harmonic energy levels and volumes of fluid.

2. The apparatus of claim 1, wherein the transducer comprises a curved single active piezo-electric element, shaped to form a sector of a sphere or cone like sound beam.

3. The apparatus of claim 1, wherein the first frequency is a fundamental ultrasound frequency.

4. The apparatus of claim 1, wherein the processor component is further configured to:
   determine, based on the determined volume, whether a threshold volume has been reached.

5. The apparatus of claim 4, wherein the processor component is further configured to:
   provide an indication in response to determining that the threshold volume has been reached.

6. The apparatus of claim 1, wherein when transmitting at least a first ultrasound signal, the transducer is configured to:
   transmit a plurality of first ultrasound signals,
   the receiver component is configured to:
      receive a plurality of first echo signals corresponding to the plurality of first ultrasound signals, and
   the processor component is configured to:
      average the received plurality of first echo signals.

7. The apparatus of claim 6, wherein when transmitting at least a second ultrasound signal, the transducer is configured to:
   transmit a plurality of second ultrasound signals,
   the receiver component is configured to:
      receive a plurality of second echo signals corresponding to the plurality of second ultrasound signals, and
   the processor component is configured to:
      average the received plurality of second echo signals.

8. The apparatus of claim 1, further comprising:
   a memory configured to store the table.

9. A method for measuring the volume of fluid in a human or animal body cavity using a non-invasive, ultrasound echo technique, comprising:
   using a transducer to:
      transmit at least a first ultrasound signal at a first power level into the body such that the at least first ultrasound signal reaches a portion of the body cavity, the body cavity being at least partially empty of the fluid such that the respective volumes of the body cavity and the fluid are different from one another; and
      transmit at least a second ultrasound signal having a first frequency and at a second power level higher than the first power level such that the at least second ultrasound signal reaches the portion of the body cavity;
   receiving ultrasound echo signals from the body cavity for the at least first and the at least second ultrasound signals;

determining a reference signal based on the at least first ultrasound signal and the received at least first ultrasound echo signal;
determining an energy level of a harmonic component of the received at least second ultrasound echo signal, wherein the harmonic component corresponds to at least a second harmonic having at least two times the first frequency;
re-scaling the reference signal based on an increase in power level between the first power level and the second power level; and
determining the volume of the fluid in the body cavity based on the determined energy level of the harmonic component and the re-scaled reference signal, wherein determining the volume comprises accessing a table storing correspondences between harmonic energy levels and volumes of fluid.

10. The method of claim 9, further comprising:
determining, based on the determined volume, whether a threshold volume has been reached.

11. The method of claim 10, further comprising:
providing an indication in response to determining that the threshold volume has been reached.

12. The method of claim 9, wherein the transmitting at least a second ultrasound signal comprises:
transmitting a plurality of second ultrasound signals, and wherein the receiving ultrasound echo signals comprises:
receiving a plurality of second echo signals corresponding to the plurality of second ultrasound signals, the method further comprising:
averaging the received plurality of second echo signals.

13. The method of claim 12, wherein the transmitting at least a first ultrasound signal comprises:
transmitting a plurality of first ultrasound signals, and wherein the receiving ultrasound echo signals comprises:
receiving a plurality of first echo signals corresponding to the plurality of first ultrasound signals, the method further comprising:
averaging the received plurality of first echo signals.

14. The method of claim 9, further comprising:
generating and storing the table in a memory.

* * * * *